United States Patent [19]

Hoshina et al.

[11] Patent Number: 5,571,674
[45] Date of Patent: Nov. 5, 1996

[54] DNA OLIGOMERS FOR USE IN DETECTION OF CAMPYLOBACTER PYLORI AND METHODS OF USING SUCH DNA OLIGOMERS

[75] Inventors: Sadayori Hoshina, Tokyo, Japan; I. Bernard Weinstein, Englewood, N.J.

[73] Assignee: The Trustees of Columbia University in the City of New York, New York, N.Y.

[21] Appl. No.: 227,475

[22] Filed: Apr. 14, 1994

Related U.S. Application Data

[63] Continuation of Ser. No. 672,691, Mar. 18, 1991, abandoned, which is a continuation-in-part of Ser. No. 408,881, Sep. 18, 1989, abandoned.

[30] Foreign Application Priority Data

Sep. 18, 1990 [JP] Japan .................................... 2-246383

[51] Int. Cl.$^6$ .............................. C12P 19/34; C12Q 1/68
[52] U.S. Cl. ................ 435/6; 435/91.2; 935/77; 935/78
[58] Field of Search ................ 435/6, 91.2; 935/77, 935/78

[56] References Cited

U.S. PATENT DOCUMENTS

| | | | |
|---|---|---|---|
| 4,683,195 | 7/1987 | Mullis et al. | 435/6 |
| 4,851,330 | 7/1989 | Kohne | 435/6 |

OTHER PUBLICATIONS

Olwe et al., Molecular & Cellular Probes 2:47–57 (1988).
Romanwk et al., J. Bact. 169(5);2137–2141 (May 1987).

*Primary Examiner*—Stephanie W. Zitomer
*Attorney, Agent, or Firm*—John P. White

[57] ABSTRACT

This invention provides a DNA oligomer having the sequence 5'GGACATAGGCTGATCTCTTAGC3' (SEQ ID NO: 1) and which is complementary to *Campylobacter pylori* 16S ribosomal RNA sequences, for use as a probe to detect *Campylobacter pylori*.

This invention also provides DNA oligomers having the sequences 5'GCGCAATCAGCGTCAGGTAATG3' (SEQ ID NO: 2) and 5'GCTAAGAGATCAGCCTATGTCCC3' (SEQ ID NO: 3) and which are complementary to certain *Campylobacter pylori* 16S ribosomal RNA sequences, for use as polymerase chain reaction primers for the detection of *Campylobacter pylori*.

This invention also provides a method for producing species-specific bacterial or protozoan DNA oligomers encoding 16S ribosomal RNA by means of the polymerase chain reaction for use as species-specific probes and PCR primers, and methods for detection and identification of bacteria and protozoa.

Further, this invention provides a DNA oligomer having the sequence 5'ACGGGCGGTGTGTGC3' (SEQ ID NO: 4).

15 Claims, 21 Drawing Sheets

FIGURE 4

SEQ. ID. NO. 1

CPC 5' G-G-A-C-A-T-A-G-G-C-T-G-A-T-C-T-C-T-T-A-G-C 3'

FIGURE 7

SEQ. ID. NO. 5

16SRRI    5'   C-A-G-C-A-G-C-C-G-C-G-G-T-A-A-T-A-C     3'

SEQ. ID. NO. 6

16SRRII   5'   C-C-G-T-C-A-A-T-T-C-C-T-T-T-G-A-G-T-T-T   3'

FIGURE 11

SEQ. ID NO. 7

```
ATCTTGCGACCGTACTCCCCAGGCGGGATGCTTAATGCGT      (1-40)
TACGTGCATTACTGGAGAGACTAAGCCCTCCAACAACTAG      (41-80)
CATCCATCGTTTAGGGCGTGGACTACCAGGGTATCTAATC      (81-120)
CTGTTTGCTCCCCACGCTTCGCGCAATCAGCGTCAGGTAA      (121-160)
TGTTCAGCAGGTCGCCCTTCGCAATGAGTATTCCTG          (161-195)
```

FIGURE 12

SEQ. ID. NO. 2

CPB    5'    G-C-G-C-A-A-T-C-A-G-C-G-T-C-A-G-G-T-A-A-T-G    3'

SEQ. ID. NO. 3

C Sense    5'    G-C-T-A-A-G-A-G-A-T-C-A-G-C-C-T-A-T-G-T-C-C    3'

FIGURE 19B

SEQ. ID NO. 8

```
  1  CTTAATGCGN  TAGGACAGCA  CTAAGGGGCG  GAACCCCCT  AACACTTAGC
 51  ACTCATCGTT  TACGGCGTGG  ACTACCAGGG  TATCTAATCC  TGTTTGATCC
101  CCACGCTTTC  GCACATCAGC  GTCAGTTACA  GACCAGAAAG  TCGCCTTCGC
151  CACTGGTGTT  CCTCCATATC  TCTGCGCATT  TCACCGCTAC  ACATGGGAAT
201  TCCACTTTCC  TCTTCTGCAC  TCAAGTTGTT  CCAGTTTCGC  AGATNGACCC
251  TNCACGGGTT  NNNNCNGTGG  GNTTTCACAT  CAGACTTAAA  AAACCGNCTA
301  AGNGNNGTTT  TNNGCCAATA  ANNCCNGNNA  ATGGTNNCNN  CNNNNTTTC
351  GNNGCATGTG  GGNGGGGNGG  NNNNNNNNNN  GGNNNGCGNN  NNNNNNNNNG
401  G
```

DNA OLIGOMERS FOR USE IN DETECTION OF CAMPYLOBACTER PYLORI AND METHODS OF USING SUCH DNA OLIGOMERS

The invention described herein was made in the course of work under Grant No. NCI CA 021111 from the National Institutes of Health. The U.S. Government has certain rights in this invention.

This application is a continuation of U.S. application Ser. No. 07/672,691, filed Mar. 18, 1991, now abandoned, which is a continuation-in-part of U.S. application Ser. No. 408,881, filed Sep. 18, 1989 now abandoned, the contents of all of which are hereby incorporated by reference into the subject application.

BACKGROUND OF THE INVENTION

Throughout this application various publications are referenced by Arabic numerals. Full citations for these references may be found at the end of the specification immediately preceding the claims. The disclosure of these publications in their entireties are hereby incorporated by reference into this application to describe more fully the state of the art to which this invention pertains.

This invention relates to the detection and identification of protozoan and bacterial species, for example, the pathogenic bacterium *Campylobacter pylori*, by use of probes for 16S ribosomal RNA, and by use of the polymerase chain reaction (PCR).

Sensitive, rapid and reliable assays for the detection of specific microorganisms are very useful both for medical diagnostic purposes, and in the context of cell and tissue culture. Assays which involve culturing contaminating microorganisms can be time-consuming.

Assays based on the direct detection of species-specific DNA sequences in a sample using DNA probes avoid culturing, but can be hampered by the rarity of specific DNA sequences relative to the whole genome of a target microorganism and the consequent difficulty of obtaining sufficient amounts of specific DNA sequences for a successful assay. (1)

One means of overcoming these problems is amplification of DNA sequences by use of the polymerase chain reaction. The abundance of a specific DNA sequence can be increased for subsequent analysis by a factor of $10^6$ with this technique, which has been used for such purposes as the detection of abnormalities in human genes, DNA sequencing, and detection of viral pathogens (1).

Applicants' invention provides a means for detecting protozoan and bacterial species in a sample of, for example, culture medium, or in a tissue specimen, by use of particular primers for the polymerase chain reaction which are homologous to certain highly conserved sequences of DNA coding for the 16S subunit of ribosomal RNA. Bacterial species encode ribosomal RNAs which are functionally and evolutionarily conserved. The nucleotide sequences of bacterial 16S ribosomal RNAs diverge in regions termed "catalogs" (2). Bacterial 16S ribosomal RNAs possess three catalogs, connected by highly conserved "universal" sequences (3). Each catalog consists of approximately 400 nucleotides (25% of the 16S RNA). Phylogenetic classifications of species have been made by comparing "oligonucleotide catalogs" of bacterial 16S ribosomal RNAs. These regions provide targets for clinical detection and diagnoses based on molecular hybridization techniques (4).

Lane (3) described these universal sequences, which were able to bind to 16S ribosomal RNA templates from over fifty microorganisms, both prokaryotic (such as bacteria and eukaryotic (such as protozoans). None of the references cited disclose the use of these universal 16S ribosomal RNA sequences as PCR primers for 16S ribosomal DNA catalogs.

Another means of overcoming the problems outlined above is to use probes that detect ribosomal RNA instead of DNA, because ribosomal RNA is abundant in the cytoplasm of all types of cells (71% of total cell RNA). Applicants' invention discloses a method for the production of species-specific DNA probes for the detection of protozoa or bacteria using PCR amplification of the species-specific sequences that exist between the binding sites of the universal 16S ribosomal RNA PCR primers; i.e., the "oligonucleotide catalogs" described above. This method may be also be used to produce species-specific PCR primers.

These assay methods provide rapid, sensitive, and efficient means of detecting bacterial or protozoan contamination of a sample or a specimen.

*Campylobacter pylori* is a bacterial strain thought to play an important causative role in chronic antral gastritis and gastric peptic ulcer diseases (5,6). *C. pylori* thrives on the surface of the stomach and produces ureases which neutralize hydrochloric acid. Diagnostic methods of detection of *C. pylori*, which could play an important role in the prevention and improvement of these disorders, would therefore be very significant.

Recent studies have revealed that the gastric mucosa of patients undergoing gastroduodenoscopy for upper abdominal complaints is often colonized by *Campylobacter pylori*. The presence of *C. pylori* has been closely associated with histologically proven gastritis and peptic ulcers (for review, see reference (7). Rauws (8) has shown a relationship between *C. pylori* infection and active chronic gastritis, and has demonstrated ultimate normalization of gastric mucosa after successful eradication of *C. pylori*. Since eradication of this organism from the gastric mucosa alleviates symptoms, early detection and treatment is important (9).

At present the urease test is the conventional method for detecting *C. pylori*, however false-positive and false-negative results are sometimes encountered (10, 11, 12, 13). To overcome these potential misdiagnoses, applicants disclose more accurate tests for the detection of *C. pylori*.

As discussed above, ribosomal RNA is a useful target for a nucleic acid probe because of its abundance. Gen-Probe produces kits for the detection of mycoplasma species (14), and for any member of the Legionellaceae family of bacteria (15) using cDNA probes for ribosomal RNA specific to mycoplasmas, or to Legionella species. However these kits do not detect specific bacterial species, in fact their purpose is not to detect specific species but to provide a broader range of detection.

Romaniuk (6) has sequenced unique, species-specific regions of *Campylobacter pylori* 16S ribosomal RNA. Using these sequences, applicants have developed a useful and practical DNA-RNA hybridization assay for the detection and identification of *Campylobacter pylori* in the gastric mucosa. This technique utilizes a [$^{32}$P]ddATP-labeled synthetic oligonucleotide probe complementary to nucleotide sequences present in *C. pylori* 16S rna. This probe is very sensitive and reacts with all 23 strains of *C. pylori* tested. It is also highly specific since there was no cross-reactivity with any of the following heterologous organisms: *C. coli*, *C. fetus*, *C. jejuni*, *C. laridis* and *Escherichia coli*. Hybridization of the oligonucleotide probe with *C. pylori* RNA was completely inhibited by treatment of the membrane filters with RNase but not by treatment with DNase. Although a gastric mucosa tissue homogenate slightly inhibited the hybridization, as few as $10^4$ *C. pylori* cells can be detected even in the presence of 5 mg of gastric mucosa.

Applicants have also developed a procedure for the detection of *Campylobacter pylori* in samples using the polymerase chain reaction. PCR amplification with universal ribosomal 16S gene primers was initially used to amplify a portion of the *C. pylori* 16S ribosomal gene. After DNA sequencing of the amplified fragment, primers specific for PCR amplification of the *C. pylori* 16S ribosomal gene were designed. With these primers, *Campylobacter pylori* can be uniquely detected, even when present in small quantities, by performing a polymerase chain reaction. There is no need to identify the DNA fragments resulting from the PCR amplification, because only *Campylobacter pylori* 16S ribosomal DNA will be amplified.

This PCR assay is even more sensitive than the RNA dot blot technique described supra. Furthermore, its ease and the fact that it does not require radioisotopes make this assay promising for clinical detection of *C. pylori*.

These two assays provide a rapid, sensitive, and efficient means for detecting *Campylobacter pylori* in gastric tissue specimens.

SUMMARY OF THE INVENTION

This invention provides a DNA oligomer having the sequence 5'GGACATAGGCTGATCTCTTAGC3' (SEQ ID NO: 1) which is complementary to bacterial 16S ribosomal RNA sequences, in particular nucleotides 76 through 97 of the bacterium *Campylobacter pylori*, for use as a probe to detect *Campylobacter pylori*.

This invention also provides a DNA oligomer having the sequence 5'GCGCAATCAGCGTCAGGTAATG3' (SEQ ID NO: 2) which is complementary to the sense strand of bacterial 16S ribosomal DNA sequences, in particular nucleotides 141 through 162 of the bacterium *Campylobacter pylori*.

Additionally, this invention provides a DNA oligomer having the sequence 5'GCTAAGAGATCAGCCTATGTCC3' (SEQ ID NO: 3) which is complementary to the antisense strand of bacterial 16S ribosomal DNA sequences, in particular those of the bacterium *Campylobacter pylori*.

This invention also provides a method for producing species-specific bacterial or protozoan 16S ribosomal DNA oligomers complementary to species—specific 16S ribosomal RNA sequences by means of the polymerase chain reaction (PCR). In one embodiment the bacterium is *Campylobacter pylori*.

This invention further provides a method for detecting bacteria or protozoa in a sample comprising amplifying bacterial or protozoan DNA encoding 16S ribosomal RNA by means of the polymerase chain reaction and detecting the resulting DNA. In one embodiment the bacterium is *Campylobacter pylori*.

This invention also provides a method for identifying bacteria or protozoa present in a sample comprising amplifying bacterial or protozoan DNA encoding 16S ribosomal RNA by means of the polymerase chain reaction and identifying the resulting DNA.

This invention also provides a DNA oligomer having the sequence 5'ACGGGCGGTGTGTGC3' (SEQ ID NO: 4).

BRIEF DESCRIPTION OF FIGURES

FIG. 4 Synthetic Probe CPC. The synthetic deoxyribonucleotide oligomer probe CPC (5'GGACATAGGCTGATCTCTTAGC3') (SEQ ID NO: 1) homologous to the 16S ribosomal RNA of *C. pylori*, was used in DNA-RNA dot blot experiments.

FIG. 7 Universal Primers. The universal primers 16S RRI (5'CAGCAGCCGCGGTAATAC3') (SEQ ID NO: 5) corresponding positions 519–536 of *E. coli* 16S ribosomal RNA and RRII (5'CCGTCAATTCCTTTGAGTTT3' (SEQ ID NO: 6)) corresponding to positions 907–926 of *E. coli* 16S ribosomal RNA were used for PCR amplification of bacterial 16S rna genes.

FIG. 11 DNA Sequence Analysis of PCR Amplified C. pylori 16S rRNA Gene. A region of the 16S rRNA gene from C. pylori strain ATCC 43526 was PCR amplified using the universal primers described in the legend to FIG. 7. Dideoxy DNA sequencing was performed using $^{32}$P-labelled 16SRRII as the sequencing primer.

FIG. 12 C. pylori Species-Specific PCR Primers. PCR amplification was performed using the C. pylori species-specific primers CPB (5'GCGCAATCAGCGTCAGG-TAATG3') (SEQ ID NO: 2) complementary to positions 141–162 of the sequence shown in FIG. 11, and C- sense (5'GCTAAGAGATCAGCCTATGTCC3') (SEQ ID NO: 3).

FIGS. 19A–B. 16SrDNA Sequence of Staphylococcus ATCC 25923 after DNA Amplification.

DETAILED DESCRIPTION OF THE INVENTION

Figure 1:
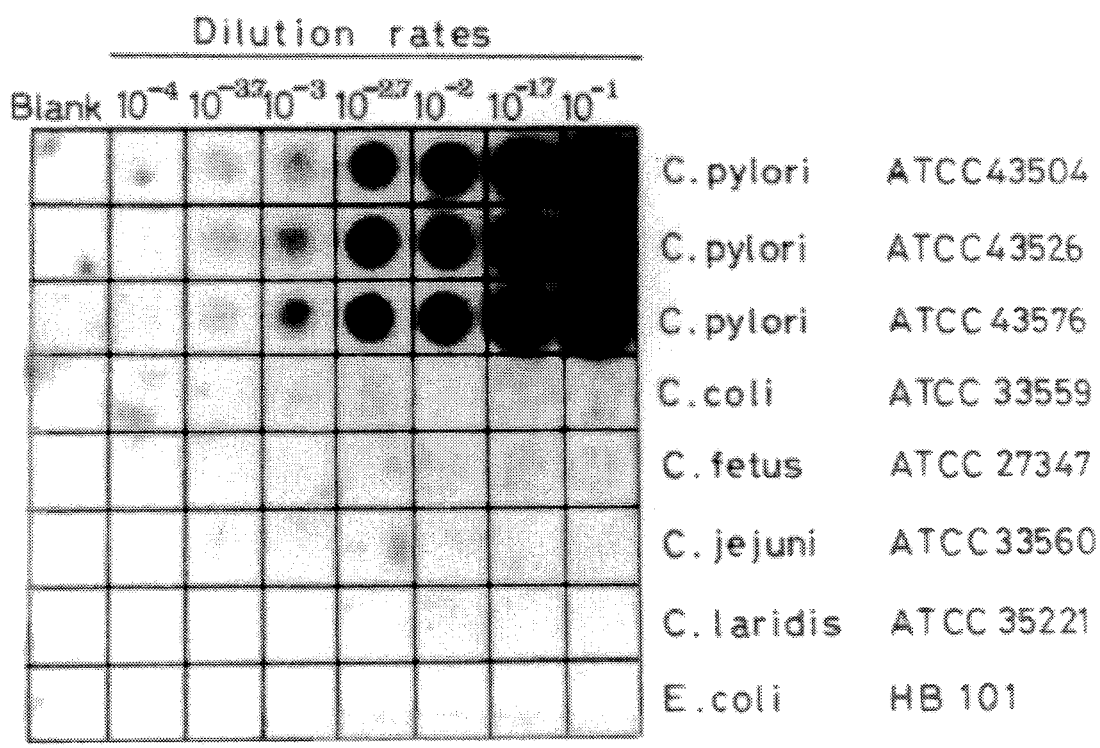
FIG. 1 Photograph Showing Species-Specific and Dose-Response Hybridization Studies with the Oligonucleotide Probe to *Campylobacter pylori*. Bacterial cells were suspended in saline, adjusted to a concentration of 0.1 OD (660 nm), and then diluted with 5M GED solution. One hundred μl of each dilution was filtered onto the membrane filter and hybridized with the $^{32}$P-labeled oligonucleotide probe.

This invention concerns a DNA oligomer having the sequence 5'GGACATAGGCTGATCTCTTAGC3' (SEQ ID NO: 1) which is complementary to bacterial 16S ribosomal RNA sequences, in particular nucleotides 76 through 97 of the bacterium Campylobacter pylori. This DNA oligomer may be labelled with a detectable marker selected from a group consisting of a radiolabelled molecule, a fluorescent molecule, an enzyme, or a ligand. The DNA oligomer is labelled with $^{32}$P[ddATP]. This labelled oligomer may be used as a probe for Campylobacter pylori.

This invention also concerns a DNA oligomer having the sequence 5'GCGCAATCAGCGTCAGGTAATG3' (SEQ ID NO: 2) which is complementary to the sense strand of DNA encoding bacterial 16S ribosomal RNA sequences, in particular nucleotides 141 through 167 of the bacterium Campylobacter pylori 16S ribosomal RNA.

This invention further concerns a DNA oligomer having the sequence 5'GCTAAGAGATCAGCCTATGTCC3' (SEQ ID NO: 3) which is complementary to the antisense strand of DNA encoding bacterial 16S ribosomal RNA sequences, in particular those of the bacterium Campylobacter pylori.

The oligomer whose sequence is 5'GCGCAATCAGCGT-CAGGTAA3' (SEQ ID NO: 2) and the DNA oligomer whose sequence is 5'GCTAAGAGATCAGCCTATGTCC3' (SEQ ID NO: 3) may be used in conjunction as primers for the polymerase chain reaction, resulting in amplification of DNA sequences encoding 16S ribosomal RNA of Campylobacter pylori.

This invention also provides a method for producing species-specific DNA oligomers encoding bacterial or protozoan 16S ribosomal RNA sequences comprising contacting isolated bacterial or protozoan DNA with DNA oligomers which are polymerase chain reaction primers and are complementary to DNA sequences encoding universal bacterial and protozoan 16S ribosomal RNA sequences, such universal sequences being located at the 3' and 5' ends of species-specific DNA encoding species-specific bacterial or protozoan 16S ribosomal RNA, under conditions suitable for a polymerase chain reaction so as to amplify the bacterial or protozoan species-specific DNA lying between the binding sites of the DNA oligomers, and isolating the resulting species-specific bacterial or protozoa DNA sequences. Probes for the 16S ribosomal RNA of specific bacteria or protozoa may be made by labelling the species-specific DNA oligomers with a detectable marker selected from a group consisting of a radio-labelled molecule, a fluorescent molecule, an enzyme, or a ligand. Multiple copies of the species-specific DNA oligomers may be made on a DNA synthesizer or produced by recombinant DNA techniques, by methods well known in the art.

This invention also provides a method for producing DNA oligomers encoding Campylobacter pylori 16S ribosomal RNA sequences comprising exposing isolated Campylobacter pylori DNA to DNA oligomers which are polymerase chain reaction primers and are complementary to DNA sequences encoding universal bacterial and protozoan 16S ribosomal RNA sequences, such universal sequences being located at the 3' and 5' ends of species-specific DNA encoding C. pylori species-specific 16S ribosomal RNA, under conditions suitable for a polymerase chain reaction so as to amplify the Campylobacter pylori species-specific DNA lying between the binding sites of the DNA oligomers, and isolating the resulting Campylobacter pylori species-specific DNA sequences. Probes for the 16S ribosomal RNA of Campylobacter pylori may be made by labelling the species-specific Campylobacter pylori DNA oligomers with a detectable marker selected from a group consisting of a radio-labelled molecule, a fluorescent molecule, an enzyme, or a ligand. Multiple copies of the species-specific *Campylobacter pylori* DNA oligomers may be made on a DNA synthesizer or produced by recombinant DNA techniques, by methods well known in the art.

The present invention also concerns a method for detecting in a sample the presence of specific bacteria or protozoa comprising exposing the sample to an agent which lyses micro-organisms, contacting the sample with a probe for the 16S ribosomal RNA of a specific bacterium or protozoan so as to produce a hybrid consisting of the probe and complementary species-specific 16S ribosomal RNA sequences of the specific bacterium or protozoan, removing unbound probe, and detecting the hybrid by the means appropriate to the type of marker with which the probe is labelled. The sample may be maintained under sterile conditions so that contamination by microorganisms not originally present in sample is avoided. The sample may further be a tissue specimen, and the method therefore provides a germ-free clinical test for the detection of specific microorganisms in the tissue.

The invention further concerns a highly sensitive method for detecting the presence of bacteria or protozoa in a sample of a isolated DNA comprising contacting the sample with DNA oligomers which are polymerase chain reaction primers and are complementary to DNA sequences encoding universal bacterial and protozoan 16S ribosomal RNA sequences, such universal sequences being located at the 3' and 5' ends of species-specific DNA encoding species-specific bacterial or protozoan 16S ribosomal RNA, under conditions suitable for a polymerase chain reaction so as to amplify the bacterial or protozoan species-specific DNA lying between the binding sites of the DNA oligomers, and detecting the resulting species-specific bacterial or protozoan DNA sequences. The detection may be accomplished by gel electrophoresis and ethidium bromide staining of the species-specific bacterial or protozoan DNA sequences in the gel. The detection may also be accomplished by calorimetric methods known in the art. The sample may be maintained under sterile conditions to avoid contamination with microorganisms not originally present in the sample. The sample may be a sterile tissue specimen, and the method therefore provides a germ-free clinical test for the detection of microorganisms in the tissue. The specific bacteria or protozoa present in the sample may be identified by restriction mapping by methods known in the art the species-specific bacterial or protozoan DNA sequences and comparing the resulting map to known bacterial or protozoan restriction maps. The specific bacteria or protozoa present in a sample may be identified by sequencing by methods known in the art the species-specific bacterial or protozoan DNA sequences and comparing the resulting sequences to known bacterial or protozoan sequences. The sample may be maintained under sterile conditions to avoid contamination by microorganisms not originally present in the sample. The sample may be a tissue specimen, in which case the method provides a germ-free clinical test for the identification of microorganisms in the tissue.

The invention further concerns a highly sensitive method for detecting the presence of specific bacteria or protozoa in a sample of isolated DNA comprising contacting the sample with DNA oligomers which are polymerase chain reaction primers and are complementary to DNA sequences encoding species-specific bacterial or protozoan 16S ribosomal RNA sequences under conditions suitable for a polymerase chain reaction, so as to amplify the bacterial or protozoan species-specific DNA lying between the binding sites of the DNA oligomers, and detecting the resulting species-specific bacterial or protozoan DNA sequences. The detection may be accomplished by gel electrophoresis and ethidium bromide staining of the species-specific bacterial or protozoan DNA sequences in the gel. The detection may also be accomplished by colorimetric methods known in the art. The sample may be maintained under sterile conditions to avoid contamination with microorganisms not originally present in the sample. The sample may be a sterile tissue specimen, and the method therefore provides a germ-free clinical test for the detection of specific bacteria or protozoa in the tissue.

The present invention also concerns a method for detecting the presence of *Campylobacter pylori* in a sample comprising exposing a sample to an agent which lyses microorganisms, contacting the sample with a probe consisting of a DNA oligomer labelled with a detectable marker and having the sequence 5' GGACATAGGCTGATCTCTTAGC3' (SEQ ID NO: 1) which is complementary to *Campylobacter pylori* 16S ribosomal RNA sequences, so as to produce a hybrid consisting of the DNA oligomer and complementary *Campylobacter pylori* 16S ribosomal RNA sequences, removing unbound probe, and detecting the hybrid by the means suitable to the type of marker used. The sample may be maintained under sterile conditions to avoid contamination by microorganisms not originally present in the sample. The sample may be a tissue specimen. The tissue may be a gastric tissue, in which the presence of *Campylobacter pylori* is indicative of gastritis, and the method therefore provides a germ-free clinical test for the diagnosis of gastritis associated with *Campylobacter pylori*. The amount of Campylobacter pylori 16S ribosomal RNA present in a sample or tissue specimen may be quantified by the means appropriate to the type of marker used.

The invention concerns a method for detecting the presence of *Campylobacter pylori* in a sample comprising exposing the sample to an agent which lyses microorganisms, contacting the sample with a probe consisting of a $^{32}$P[ddATP]-labelled DNA oligomer having the sequence 5'GGACATAGGCTGATCTCTTAGC3' (SEQ ID NO: 1) which is complementary of *Campylobacter pylori* 16S ribosomal RNA sequences, so as to produce a labelled hybrid consisting of the DNA oligomer and complementary *Campylobacter pylori* 16S ribosomal RNA sequences, removing unlabelled probe, and detecting the presence of the $^{32}$P marker on the labelled hybrid. The sample may be maintained under sterile conditions to avoid contamination by microorganisms not originally present in the sample. The sample may be a sterile tissue homogenate. The tissue sample may be gastric tissue homogenate and the detection of *Campylobacter pylori* in the specimen therefore constitutes a germ-free clinical test for gastritis associated with *Campylobacter pylori*.

The invention further concerns a method for quantitating the amount of *Campylobacter pylori* 16S ribosomal RNA in a sample by exposing the sample to an agent which lyses microorganisms, contacting the sample with a membrane filter so as to bind nucleic acids in the sample to the filter, and contacting the resulting filter with a probe consisting of a $^{32}$P-labelled DNA oligomer having the sequence 5'GGACATAGGCTGATCTCTTAGC3' (SEQ ID NO: 1) and which is complementary to *Campylobacter pylori* 16S ribosomal RNA under conditions such that the DNA oligomer forms a hybrid with complementary *Campylobacter pylori* 16S ribosomal RNA sequences, removing unbound probe, and determining the amount of $^{32}$P-labelled hybrid present on the filter by measuring counts of radioactivity in a scintillation counter. The sample may be a tissue specimen which may be maintained under sterile conditions to avoid contamination by microorganisms not originally present in the specimen. The tissue may be gastric tissue, and qualification of *Campylobacter pylori* 16S ribosomal RNA in the specimen can be used to monitor the progress of *Campylobacter pylori*-associated gastritis treatment.

The invention further concerns a highly sensitive method for detecting the presence of *Campylobacter pylori* in a sample of isolated DNA comprising contacting the sample with a DNA oligomer having the sequence 5'GCGCAAT-CAGCGTCAGGTAATG3' (SEQ ID NO: 2) and the DNA oligomer having the sequence 5'GCTAAGAGATCAGC-CTATGTCC3' (SEQ ID NO: 3) both of which are polymerase chain reaction primers and are complementary to DNA sequences encoding *Campylobacter pylori* 16S ribosomal RNA sequences, under conditions suitable for a polymerase chain reaction, so as to amplify the *Campylobacter pylori*-specific DNA lying between the binding sites of the DNA oligomers, and detecting the resulting *Campylobacter pylori*-specific DNA sequences. The detection may be accomplished by gel electrophoresis and ethidium bromide staining of the *Campylobacter pylori*-specific DNA sequences in the gel. The detection may also be accomplished by calorimetric methods known in the art. The sample may be maintained under sterile conditions to avoid contamination with microorganisms not originally present in the sample. The sample may be a sterile tissue specimen, and the method therefore provides a germ-free clinical test for the diagnosis of gastritis associated with *Campylobacter pylori*.

This invention also provides a DNA oligomer having the sequence 5'ACGGGCGGTGTGTGC3' (SE ID NO: 4).

This invention is illustrated in the Experimental Details section which follows. This section is set forth to aid an understanding of the invention but is not intended to, and should not be construed to, limit in any way the invention as set forth in the claims which follow.

EXPERIMENTAL DETAILS

EXAMPLE 1

MATERIALS AND METHODS

Bacterial strains: All strains with ATCC numbers were purchased from American Type Culture Collection (ATCC; Rockville, Md.). The sources of the other strains are described in the footnote of Table 1. The medium, brain heart infusion agar supplemented with 5% sheep blood (Gibco Diagnostics, Madison, Wis.) was used for the growth of all of the Campylobacter strains. The plates were incubated at 37° C. in microaerophilic conditions provided by a Campy Pak envelope (BBL Microbiological Systems, Cockeysville, Md.) in a GasPak jar (BBL) without catalyst.

Synthetic oligonucleotide probe: The oligonucleotide probe sequence, 5'-d(GGACATAGGCTGATCTCTTAGC) (SEQ ID NO: 1), is complementary to the 16Sr RNA sequences of *C. pylori* reported by Romaniuk (9). This oligonucleotide was synthesized on a DNA synthesizer (Applied Biosystems 380 A; ) and purified by polyacrylamide gel electrophoresis. The 3'-end of the oligomer was labeled using [a-$^{32}$P]ddATP ($^-$3000 Ci/m mol; Amersham, Arlington Heights, Ill.) and terminal deoxynucleotidyl transferase (3'-end labelling kit; Amersham) under the conditions suggested by the supplier. The specific activity of the labeled oligonucleotide probe was $8.8 \times 10^6$-$1.8 \times 10^8$ cpm/µg.

Preparation of dot blot: Fresh bacterial cells were suspended in 0.9% NaCl at a concentration of OD=1 (660 nm) and then dissolved and diluted with 5M guanidine thiocyanate (Fluka Chemical Corp. Ronokonkoma, N.Y.), 0.1M EDTA (pH=7.0), 10 mM dithiothreitol solution (GED solution). One hundred microliters of bacterial cell lysate, unless otherwise noted, was filtered onto a nylon membrane filter (Gene Screen Plus; E. I Du Pont de Nemours & Co., Wilmington, Del.) by vacuum aspiration with a microsample filtration manifold (Minifold I; Schleicher & Schnell, Dassel, Federal Republic of Germany), and then the filters were air-dried. In the experiments shown in FIG. 2, filters were treated with DNase (DNase type 1 [Boehringer Mannheim Biochemicals, Indianapolis, Ind.], 46 unit/ml, in 50 mM Tris-hydrochloride, 10mM MgSO$_4$, 0.1 mM dithiothreitol and 50 µg/ml of bovine serum albumin fraction v), or they were treated with RNase (RNase A [Boehringer Mannheim], 20 µg/ml of 2×SSC [1×SSC=0.15M NaCl plus 15 mM sodium citrate]) at 37° C. for 30 min. The filters were then washed 3 times with 2×SSC at room temperature for 5 min. and allowed to air dry before hybridization.

In order to determine a possible inhibitory effect of gastric mucosa on the assay (FIG. 3) cultured cells of *C. pylori* ATCC 43579 were mixed with different amounts of rat gastric tissue, homogenized in 5M GED solution using a polytron homogenizer, filtrated onto the membrane filter and then hybridized with the probe. The amount of rat gastric tissue used ranged from 0 to 5 mg, since the average clinical biopsy sample is usually less than 5 mg.

Biopsy specimens of gastric mucosa were homogenized in 0.5 ml of 5M GED solution and filtrated onto membrane filters as described above.

Hybridization method: The hybridization and subsequent washing were performed by the method of Farr, C. T., et al. (17). The optimum time and temperature parameters for the incubations were determined in preliminary experiments. Briefly, the prehybridization solution (0.08 ml/cm$^2$ of filter) contained 5M tetramethylammonium chloride, 50 mM Tris-hydrochloride (pH 7.5), 2mM EDTA, 0.3% sodium dodecyl sulfate (SDS), 100 µg/ml of denatured salmon sperm DNA, and 5×Denhardt's solution (1×Denhardt's solution=0.02% bovine serum albumin, 0.02% polyvinylpyrrolidone, and 0.02% Ficoll). This solution was transferred to a plastic bag containing the filter and the plastic bag was sealed and incubated, with constant agitation, for 30 to 60 min at 50° C. Radioactive probes were then added to the bags at a concentration of 10 ng/ml. The bags were incubated at 50° C. for 2 hrs. After hybridization, the filters were washed twice in 2×SSPE (1×SSPE=150 mM NaCl, 10 mM NaHPO$_4$, and 1 mM EDTA [pH7.0]), 0.1% SDS at room temperature for 10 minutes, and then twice in the hybridization solution without salmon sperm DNA and Denhardt's solution, at 55° C. for 15 min. Hybridization with the probe was detected by autoradiography with X-Omat AR films (Eastman Kodak Co., Rochester, N.Y.) exposed for 1–2 days at –70 ° C. with intensifying screens. For liquid scintillation counting, the filters were cut up into squares, placed into scintillation vials, and counted in Hydrofluor™ scintillant (National Diagnostics, Manville, N.J.).

Chromosomal DNA probe and whole-cell dot blot hybridization: The preparation of bacterial chromosomal DNA probes and whole-cell dot blot hybridization procedures were performed as previously described (18). Briefly, chromosomal DNAs were labeled with [α-$^{32}$P]dCTP by using nick translation procedure. The labeled chromosomal DNA probes were denatured at 100° C. in 10 mM Tris-HCl, pH 8.0, 1 mM EDTA for 5 minutes immediately before use.

Five, ten, and fifty μl of bacterial cell suspension (OD=0.1, 660 nm) were filtered onto a membrane filter by means of a microsample filtration manifold. Filters were treated twice with 0.5N NaOH for 2 minutes to release and fix the DNA to the filters, and then twice with 1M Tris-HCl (pH 7.5) for 2 minutes. The filters were allowed to air dry. The prehybridization solution (0.08 ml/cm² of filter) contained 50% formamide, 1% sodium dodecyl sulfate (SDS), 1 M NaCl and 10% dextran sulfate. The solution was transferred to a sealable plastic bag containing the filter and incubated with constant agitation for at least 15 minutes at 42° C. Denatured salmon sperm DNA and denatured radioactive probe were added to the bags before hybridization, at the concentration of 100 μg/ml and 10ng/ml, respectively. The bags were incubated overnight at 42° C. After hybridization, the filters were washed twice in 2×standard saline citrate, pH 7.0, at room temperature for 5 minutes, twice in 2×SSC and 1% SDS at 65° C. for 30 minutes, and then twice in 0.1×SSC at room temperature for 30 minutes.

Bacteriological culture and urease test: Biopsy specimens from endoscopies were inoculated onto 5% sheep blood brain heart infusion agar and incubated as described above. Biochemical identification of *C. pylori* was performed according to the manual (23). For the urease test, specimens were inoculated in urease test tubes (BBL) and incubated at room temperature for four hours. Positive samples turned the color of the medium red.

RESULTS

Figure 2:
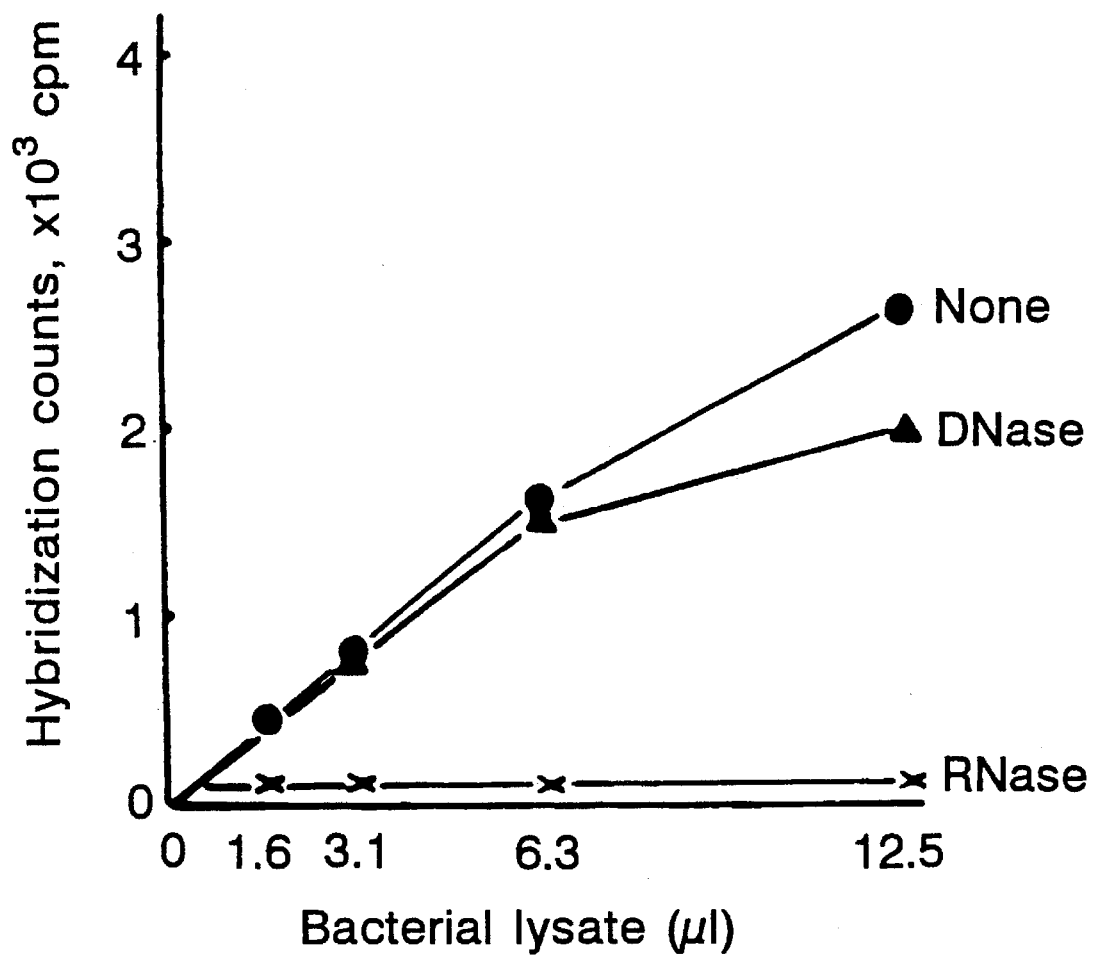
FIG. 2 Line Graph Representative of the Hybridization of the Oligonucleotide Probe to Bacterial RNA. A cell suspension of *Campylobacter pylori* ATCC 43579 (OD=0.1, 660 nm) was mixed with 4 volumes of 5M GED solution, filtered onto the membrane filter, treated with RNase A or DNase, and then hybridized with the oligonucleotide probe. Hybridization counts were measured by liquid scintillation counting.
Figure 3:
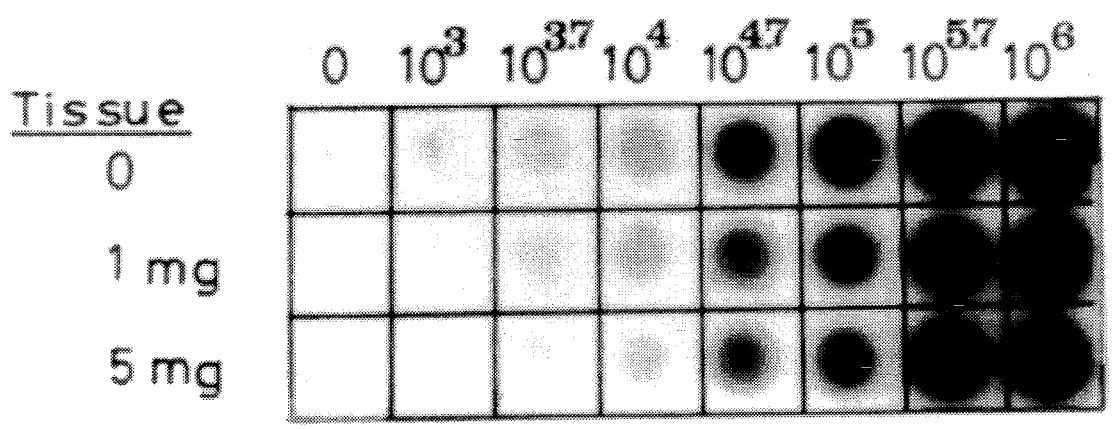
FIG. 3 Photograph Showing the Detection of *Campylobacter pylori* by the Oligonucleotide Probe in the Presence of Rat Gastric Tissue. Cultured cells of *C. pylori* ATCC 43579 were mixed with different amounts of rat gastric tissue homogenate, filtered onto the membrane filter and then hybridized with oligonucleotide probe. The amount of bacterial cells and rat gastric tissue on each dot blot were 0–$10^6$ cells and, 0, 1 and 5 mg equivalent of tissue homogenates, respectively.

We synthesized three different oligonucleotide sequence probes and tested their hybridization specificity for 3 strains of *C. pylori*, 4 strains of other Campylobacter species and 1 strain of *Escherichia coli*. One of these oligonucleotide, 5'-d(GGACATAGGCTGATCTCTTAGC), (SEQ ID NO: 1) hybridized specifically with *C. pylori* under the hybridization and washing conditions described in Materials and Methods (FIG. 1). No cross-reactivity was found. Treatment of the filters with RNase, but not DNase, completely inhibited the hybridization, indicating that this oligonucleotide hybridized with bacterial RNA (FIG. 2). The specificity of the oligonucleotide probe was tested and compared with that of chromosomal DNA probe using 20 clinical isolates of *C. pylori,* which were isolated in Peru, Australia, United States, England and Japan, and a panel of unrelated bacteria. These data are summarized in Table 1. The oligonucleotide probe reacted with all *C. pylori* strains, with no cross reactions to other bacterial strains, whereas the whole chromosomal DNA probe showed weak cross reactions with some strains of other Campylobacter species. Next, the sensitivity of this oligonucleotide probe was tested in the presence of rat gastric tissue. Cultured *C. pylori* cells were added to a sample of rat gastric tissue and homogenized in 5M GED solution using a polytron homogenizer. The homogenates were then filtered onto the membrane filter and then hybridized with the probe. Although the tissue homogenates slightly inhibited the hybridization, as few as 5×10³–10⁴ *C. pylori* cells per assay were detected by this method (FIG. 3).

Biopsy specimens obtained from fourteen patients referred for upper gastrointestinal tract endoscopy were tested for *C. pylori* infection by oligonucleotide hybridization and the results were compared with those of the urease test, direct stain, and bacteriological culture (Table 2). There was high correlation between the results obtained by oligonucleotide hybridization and the urease test: seven out of eight urease-positive patients showed positive hybridization reactions and seven out of eight urease-positive patients showed positive hybridization reactions and seven out of eight hybridization-positive specimens were urease positive.

DISCUSSION

In a recent report (18), we demonstrated that DNA—DNA hybridization with a dot blot format and ³²P-labeled probes is useful for rapid and accurate identification of intestinal Bacteroides species. Although in these studies the whole chromosomal DNA probes were specific enough to distinguish one bacterial species from the others, more highly specific non-cross reacting probes are needed for the direct detection of specific organisms in crude clinical specimens (19).

Since oligonucleotide probes are highly specific and easy to synthesize in large quantities, they are well suited for use in clinical laboratories. For example, Sommerfelt et al. (16) reported the clinical application of a highly specific synthetic oligonucleotide probe for the identification of enterotoxigenic *Escherichia coli*. Although the design of oligonucleotide probes for Campylobacter has been reported (19), the clinical application has yet to be reported. The latter study reported two synthetic oligonucleotide probes based on *C. jejuni* 16S rRNA sequences. One of these probes was unable to distinguish between *C. jejuni, C. coli* and *C. laridis*, whereas the second probe hybridized to all Campylobacter species tested. Our results are the first, to our knowledge, to describe the construction of a species specific 16S rRNA-targeted oligonucleotide probe for *Campylobacter pylori*.

A possible disadvantage of short oligonucleotide probes is that their sensitivity may be affected by minor nucleotide changes in the target sequences. Our oligonucleotide probe, however, hybridized to all of the 20 *C. pylori* strains tested, which had been isolated in 5 different countries, with no detectable cross-reactions to other bacterial strains (FIG. 1, Table 1). A whole bacterial chromosomal DNA probe, however, showed weak homology with the DNAs of *C. pylori, C. coli, C. jejuni* and *C. laridis* (Table 1), as previously reported by Romaniuk et al. (6).

Gastric biopsy specimens obtained from patients referred for upper gastrointestinal tract endoscopy were tested for *C. pylori* infection by direct oligonucleotide hybridization and the results were compared with those of bacteriological cultures, the urease test, and histological observations. A comparison of the urease test and the oligonucleotide hybridization results showed an excellent correlation between the two methods.

Although the short half life and the requirement for ³²P labeling restrict the hybridization reactions to laboratories equipped to use radioactive compounds, by adapting non-radioactive-labeling methods it should become feasible to use the oligonucleotide hybridization technique in routine clinical studies.

TABLE 1

Specific hybridization of synthetic oligonucleotide probe and chromosomal DNA probes with strains of *C. pylori*.

| Test strains | Synthetic oligonucleotide probe | Chromosomal DNA probe of *C. pylori* | |
|---|---|---|---|
| | | ATCC 43504 | ATCC 43526 |
| *C. Pylori:* | | | |
| ATCC 43504[b] | + | + | + |
| ATCC 43526[b] | + | + | + |

TABLE 1-continued

Specific hybridization of synthetic oligonucleotide probe and chromosomal DNA probes with strains of C. pylori.

| Test strains | Synthetic oligonucleotide probe | Chromosomal DNA probe of C. pylori | |
|---|---|---|---|
| | | ATCC 43504 | ATCC 43526 |
| ATCC 43579[b] | + | + | + |
| 3158[c] | + | + | + |
| 3162[c] | + | + | + |
| 3164[c] | + | + | + |
| 3265[c] | + | + | + |
| 3267[c] | + | + | + |
| 3268[c] | + | + | + |
| 3270[c] | + | + | + |
| 3271[c] | + | + | + |
| 3274[D] | + | + | + |
| 3275[c] | + | + | + |
| 17[e] | + | + | + |
| 19[e] | + | + | + |
| 20[e] | + | + | + |
| 26[e] | + | + | + |
| 35[e] | + | + | + |
| 37[e] | + | + | + |
| TX30A[f] | + | + | + |
| 60190[a] | + | + | + |
| 133C[h] | + | + | + |
| NCTC 11638[i] | + | + | + |
| E. coli ATCC 335596[b] | − | VW | ND |
| C. fetus subsp. fetus ATCC 27347[b] | − | − | ND |
| C. jejuni ATCC 33560[b] | − | VW | ND |
| C. laridis ATCC 35221[b] | − | VW | ND |
| Escherichia coli HB101 | − | − | ND |

[a]+, − and VW represented strong darkened dot (positive reaction), no visible reaction (negative reaction) and very weak reaction (cross-reaction) by autoradiography, respectively.
[b]Strains obtained from American Type Culture Collection (ATCC).
[c,d]Strains obtained from Drs. D. L. Shungu and C. Gill, originally isolated in Peru[c] and Australia[i].
[e]Strains obtained from Dr. Kin, isolated in Japan.
[f,g,h,i]Strains obtained from Dr. D. R. Morgan, originally isolated in United States[f], England[a], Peru[h] and Australia[i].
[i]Not done.

TABLE 2

Comparison of various assays for detecting Campylobacter pylori in clinical specimens.

| Patient Number | Clinical Diagnosis by Endoscopy | Oligo-nucleotide probe | Urease test | Warthin Starry Stain | Bacteriological culture |
|---|---|---|---|---|---|
| 1 | Normal | − | − | − | − |
| 2 | Gastritis | − | − | − | − |
| 3 | Gastritis | − | − | − | − |
| 4 | Gastritis | − | − | − | − |
| 5 | Gastritis | + | + | + | + |
| 6 | Gastritis | + | + | + | + |
| 7 | Gastritis | − | + | + | NT[a] |
| 8 | Gastritis | + | + | NT | + |
| 9 | Gastritis | − | − | − | − |
| 10 | Gastritis | + | − | − | − |
| 11 | Gastritis | + | + | NT | + |
| 12 | Duodenal ulcer | + | + | + | + |
| 13 | Duodenal ulcer | + | + | + | + |
| 14 | Duodenal ulcer | + | + | NT | − |

[a]Not tested.

EXAMPLE 2

MATERIALS AND METHODS

Conventional bacteriological assay. All bacterial strains with ATCC numbers were purchased from American Type Culture Collection. For subsidiary cultures of Campylobacter, brain heart infusion agar supplemented with 5% sheep blood (Gibco Diagnostics, Madison, Wis.) was used under microaerophilic conditions provided by a Campy Pak envelope (BBL Microbiological Systems, Cockeysville, Md.) in a Gas Pak jar (BBL) without catalyst. Biopsy specimens from endoscopies were inoculated in urease test tubes (BBL) and incubated at room temperature for four hours. Positive samples turned the color of the medium red.

RNA dot-blot hybridization. Synthetic oligonucleotide were synthesized with the use of an applied Biosystems Model 380A DNA synthesizer (Applied Biosystems, Foster City, Calif.). Oligonucleotide were labelled using gamma-[$^{32}$P] dATP and polynucleotide kinase. Unincorporated nucleotides were removed with Sephadex G50 spin columns. Fresh bacterial cells were suspended in saline at a concentration of $OD_{660}$=1. Bacteria were then extracted with GDE buffer (5M guanidine thiocyanate (Fluka Chemical Corp., Ronkonkoma, N.Y.), 10 Mm dithiothreitol, 0.1 M EDTA (Ph=7.0)). Biopsy specimens were homogenized with a polytron in GDE buffer. One hundred ul of each sample was spotted onto a nylon membrane filter (Gene Screen Plus: E. I. Du Pont de Nemours & Co., Wilmington, Del.) with a microsample filtration manifold (Minifold I: Schleifer and Schuell, Federal Republic of Germany).

Hybridization and subsequent washings were performed by the method of Farr, et al. (17). The hybridization solution contained 5M tetramethylammonium chloride, 50 mM Tris hydrochloride (pH 7.5), 2 mM EDTA, 0.3% SDS, 100 μg/ml denatured salmon sperm DNA, and 5×Denhardt's solution. Filters were first incubated in hybridization solution for 30–60 minutes at 50° C. The radioactive probe was then added to a concentration of 10 ng/ml, and the filters incubated at 50° C. for an additional two hours. Filters were washed twice in 2×SSPE (1×SSPE: 150 mM NaCl, 0.1% SDS, 10 mM $NaH_2PO_4$, 1 mM EDTA) at room temperature for 10 minutes, and then twice in hybridization solution, without salmon sperm DNA and Denhardt's solution, at 55°

C. for 15 minutes. Filters were then exposed to Kodak X-Omat AR film.

Preparation of biopsy and bacterial samples. Biopsy samples 1a–31a (3–4mg) were ground with a mortar and pestle and dissolved in 200 µl of sterile water. Samples 1–10 were homogenized in GDE buffer using a polytron. DNA was prepared as previously described. Bacteria were grown on appropriate nutrient plates, and individual colonies were suspended in 1×PCR buffer (see below) prior to PCR amplification.

Enzymatic amplification of DNA. DNA from biopsy samples (1 µg) was suspended in 1×PCR buffer (50 mM KCl/10 mM Tris HCl, pH8.3/1.5 mM $MgCl_2$/0.01%(W/V) gelatin), 1.25 mM dNTPs, 250 ng of each primer, and 2.5 units of Taq DNA polymerase (Perkin-Elmer Cetus, Norwalk, Conn.) to a volume of 100 µl, as previously described (24). 10 µl aliquots of bacterial suspensions were similarly prepared. Reaction samples were overlaid with 100 µl of mineral oil to prevent evaporation. DNA was amplified via the polymerase chain reaction for 30 cycles (1 minute at 94° C., 2 minutes at 55° C., 3 minutes at 72° C.) in a Perkin-Elmer Cetus Thermocycler. Amplified DNA was analyzed by electrophoresis through a native 6% polyacrylamide gel followed by staining with ethidium bromide.

Sequencing of amplified DNA. Amplification reactions (100 µl) were diluted with 2 ml of distilled water and spun through Centricon 30 columns (Amicon, Danvers, Mass.) to remove excess dNTPs and primers. Retentates were collected in 40 µl of TE buffer. Dideoxy sequencing of PCR products was performed using $^{32}$-P end-labelled primers, following the protocol of Higuchi, et al. (21). Sequencing products were loaded onto 6% polyacrylamide, 7M urea gels and electrophoresed for 2.5 hours at 1700 volts. Gels were then exposed to Kodak X-Omat film.

RESULTS

Oligonucleotide dot blot hybridization. The synthetic oligonucleotide probe CPC, shown in the legend to FIG. 4 (SEQ ID NO: 1), which was used in bacterial RNA dot blot hybridization experiments, is complementary to nucleotides 76 through 97 of C. pylori 16S rRNA. Because this sequence is specific to C. pylori 16S rRNA, the CPC probe could distinguish C. pylori from other Campylobacter species. FIG. 2 demonstrates the specificity of probe CPC for 16S rRNA from various C. pylori strains and Campylobacter species, using E. coli strain HB101 as a negative control, in a RNA dot blot hybridization experiment. CPC hybridized to RNA from the three C. pylori strains, but it did not hybridize to RNA from other Campylobacter species nor to RNA from E. coli strain HB101. The sensitivity of the CPC probe for C. pylori was determined in a titration experiment shown in FIG. 3.

Hybridization to RNA from as few as $10^3$ bacterial cells per dot could be detected. Since several thousand ribosomes exist in each bacterial cell, this translates into the need for approximately $10^6$ copies of C. pylori 16S rRNA for successful hybridization.

Figure 8:
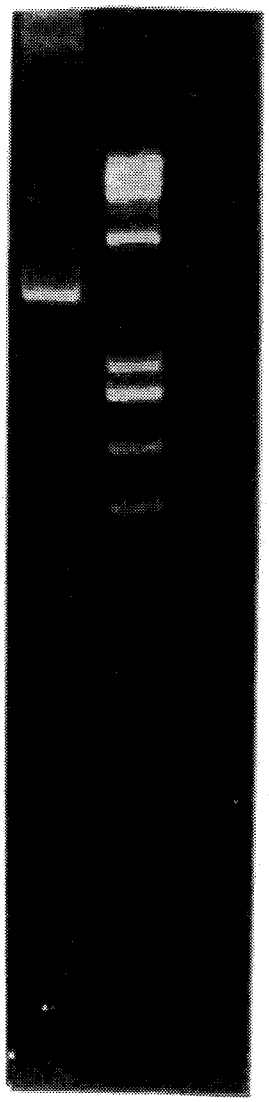
FIG. 8 Photograph of a Gel Showing a PCR Amplified *C. pylori* 16S rRNA Gene. Amplification of *C. pylori* purified DNA. Lane 1: Hae II digested μx174 DNA size marker. Lane 2: PCR amplified *C. pylori* (ATCC 43526) DNA using the universal primers described above. The major band detected in lane 2 is approximately 450 nucleotides.
Figure 9:
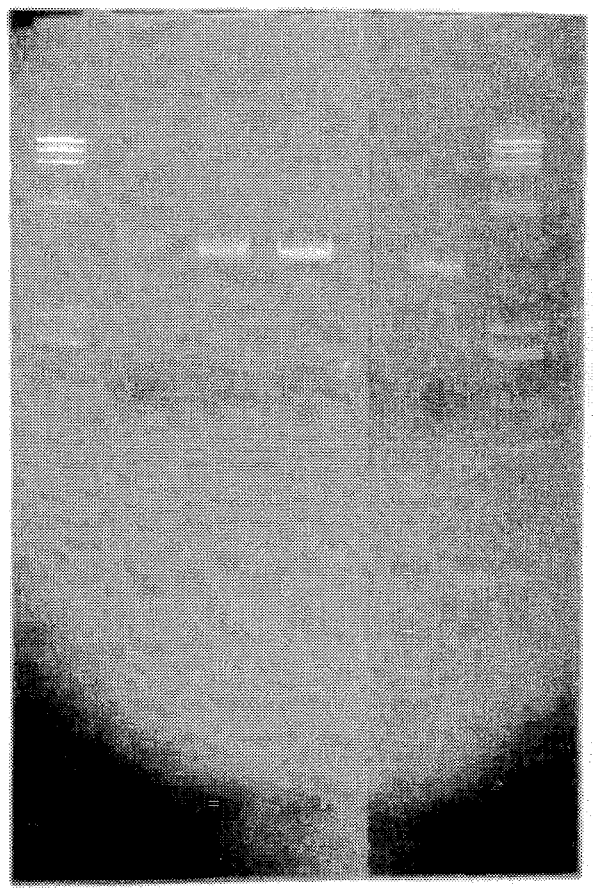
FIG. 9 Photograph of a Gel Showing PCR Amplified DNAs of Various Bacterial Strains. Amplification of various bacterial DNAs from crude lysates using the universal 16S primers. Lanes 1 and 6: Hae III digested φx174 DNA size marker. lanes 2–5: Amplification products using lysates from *E. coli* HB101; *C. fetus* ATCC 27347; *C. jejuni* ATCC 33560; *C. laridis* ATCC 35221.
Figure 10:
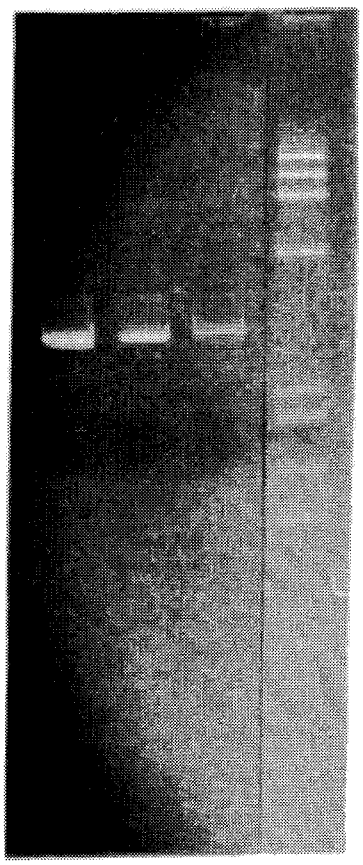
FIG. 10 Photograph of a Gel Showing PCR Amplified Sequences of *C. pylori* Strains. PCR amplification of lysates from three different *C. pylori* strains using the universal 16S primers. PCR amplification was carried out for 10 cycles in this study. Lanes 1–3: *C. pylori* strain ATCC 43504; *C. pylori* strain ATCC 43526; *C. pylori* strain ATCC 43576. Lane 4: Hae III digested φx174 DNA size marker.

Amplification by universal primers and C. pylori specific primers. Phylogenetic research has revealed universal sequences present in 16S rRNA genes which are conserved among different species of bacteria. We synthesized universal primers corresponding to positions 519 to 536 (16SRRI) and positions 907 to 926 (16SRRII) of E. coli 16S rRNA for use in the amplification of various bacterial 16S rRNA gene sequences via the PCR method. FIGS. 8–10 show the products of PCR amplification from C. pylori strain ATCC 43526 (FIG. 8), E. coli strain HB101, C. fetus strain ATCC 27347, C. jejuni strain ATCC 33560, C. laridis strain ATCC 35221 (FIG. 9), C. pylori strain ATCC 43504, and C. pylori strain 43576 (FIG. 10) using primers 16SRRI and 16SRRII.

Dideoxy sequencing of amplified DNA from C. pylori strain ATCC 43526 was performed using end-labelled 16SRRI and 16SRRII as primers. A comparison of the C. pylori sequence shown in FIG. 12 to the 16S rRNA sequences of other bacteria revealed a less conserved region between positions 141 and 162. Therefore, an oligonucleotide corresponding to this region was synthesized as a C. pylori-specific amplification primer (CPB).

Figure 13:
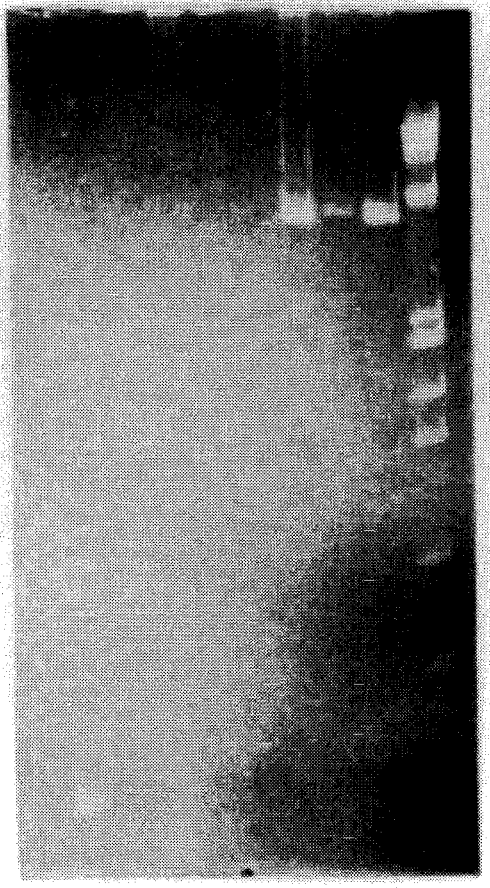
FIG. 13 Photograph of a Gel Showing Species-Specific PCR Amplified C. pylori 16S rRNA Gene. Lane 1: Hae III digested φ×174 DNA size marker. PCR amplification products of lysates from; Lanes 2–4: C. pylori strains ATCC 43526; 43504, and 43576. Lane 5: C. fetus strain ATCC 27347. Lane 6: C. jejuni strain ATCC 33560. Lane 7: C. laridis strain ATCC 33559. Lane 8: C. coli strain ATCC 33559. Lane 9: E. coli strain HB101. Lane 10: PCR buffer negative control.

FIG. 13 shows the results of PCR amplification using the C. pylori species-specific primers CPB and C sense (the complementary sequence of probe CPB), the seven bacterial strains referred to in FIG. 12, and C. coli strain ATCC 33559. While the universal primers are able to amplify fragments from all bacterial strains, the C. pylori specific primers were able to amplify only the three C. pylori strains. Therefore, primers CPB and C sense can be used for the specific amplification of C. pylori strains.

Figure 14:
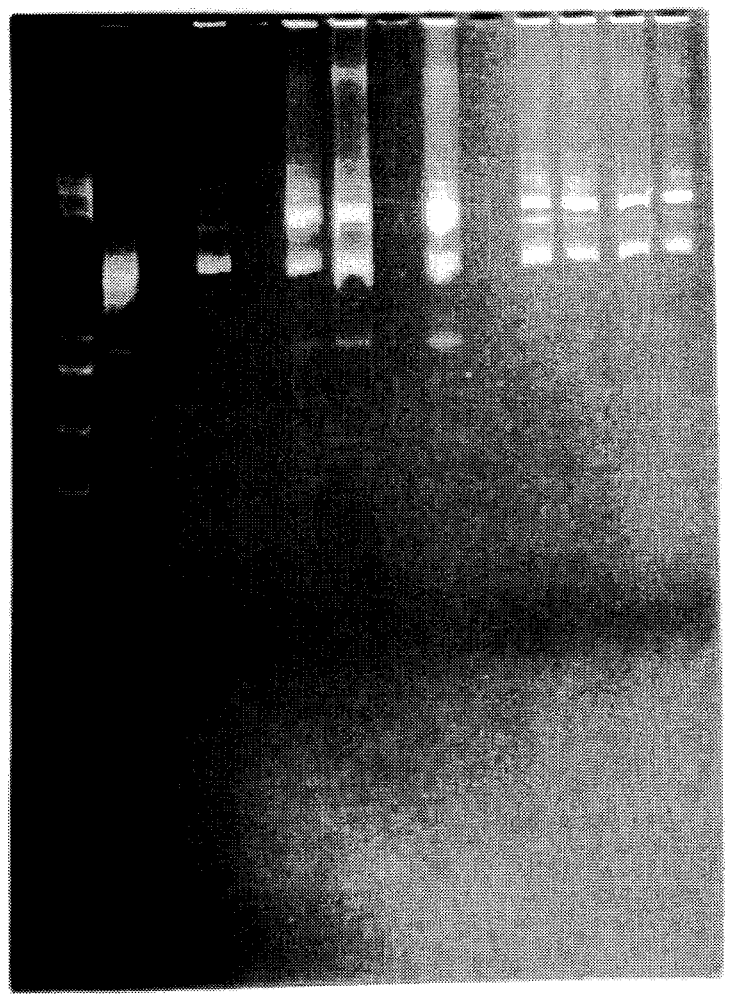
FIG. 14 Photograph of a Gel Showing PCR Amplified Human Gastric Biopsy Specimens. PCR amplification using the universal primers 16SRRI and 16SRRII. The order of lanes is as follows; Lane 1: Hae III digested φ×174 DNA size marker; Lane 2: amplified C. pylori strain ATCC 43526 DNA; Lanes 3–12: amplified DNA from gastric biopsy samples (corresponding to cases 1–10 in Table 2).
Figure 15:
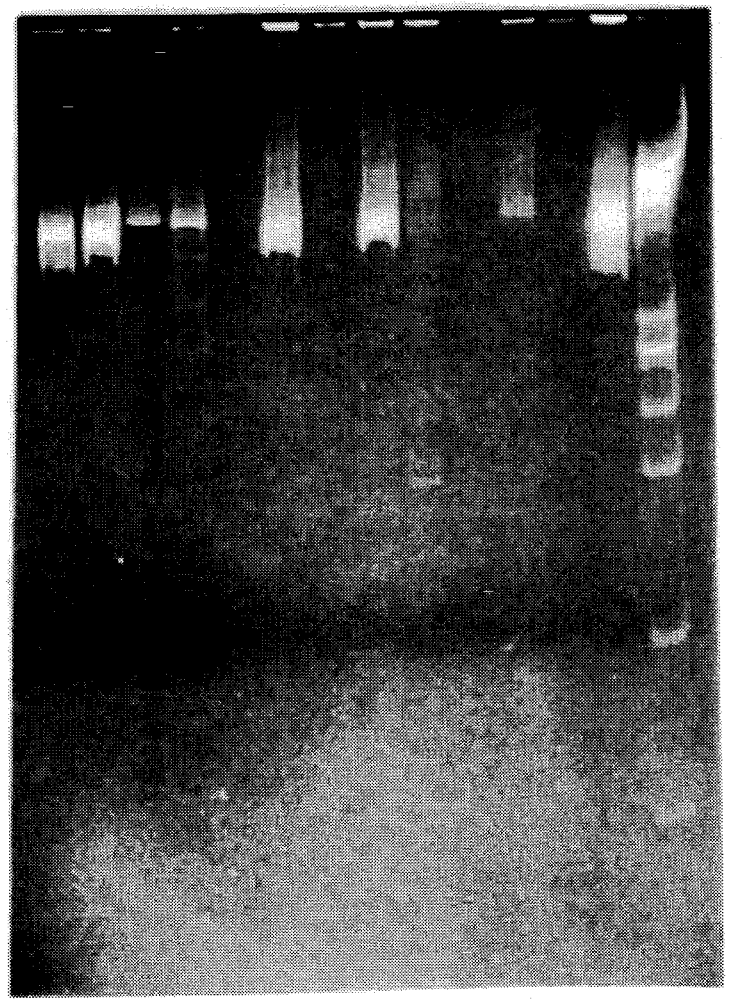
FIG. 15 Photograph of a Gel Showing PCR Amplified Human Gastric Biopsy Specimens. PCR amplification using the C. pylori-specific primers CPB and C-sense. The order of lanes is as follows; Lane 1: Hae III digested φ×174 DNA size marker; Lane 2: amplified C. pylori strain ATCC 43526 DNA; Lanes 3–12: amplified DNA from gastric biopsy samples (corresponding to cases 1–10 in Table 2).

Direct detection of C. pylori from clinical specimens. Biopsy specimens from gastric endoscopies were PCR amplified with universal primers 16SRRI and 16SRRII (FIG. 14) and with C. pylori specific primers CPB and C sense (FIG. 15), to test for the presence of bacteria in general, and C. pylori specifically. The same biopsy specimens were also subjected to the classical urease test and Warthin Starry stain to determine the relative sensitivity of each assay. Finally, the establishment of bacterial cultures from each sample was attempted.

Of the ten cases (1–10) shown in Table 2, clinical endoscopies from patients 2, 4, 7, 9, and 10 scored positive using the urease test. These five cases, along with samples from patients 6 and 8, gave rise to PCR amplification using C. pylori-specific primers, suggesting that the urease test does directly indicate the presence of C. pylori, though with a lower sensitivity than the PCR assay. These same seven cases, along with a sample from patient 3, gave rise to PCR amplification using the universal primers, providing evidence of the presence of bacteria. Samples from patients 2, 3, 4, 7, and 9 were positive in the dot blot assay, and all of these samples except sample 3 were positive in both the urease test and C. pylori specific PCR assay. Thus, the dot blot assay appears to be less sensitive than both the urease test and C. pylori-specific PCR assay. The Warthin Starry stain was positive only in samples from patients 2, 4, and 9, while bacterial cultures could only be established from samples 2, 9, and 10. A normal sample from patient 1 scored negative in all of the above assays.

Further clinical results from patients (1a–31a) with various gastrointestinal tract diseases using both the PCR assay and the urease test for the detection of C. pylori are shown in Table 3. Seven out of ten samples from patients with gastritis, and four of six samples from patients with duodenal ulcers gave rise to PCR amplification using C. pylori-specific primers. Results obtained using the urease test were positive in five out of the ten gastritis patient biopsies and three out of six duodenal ulcer biopsies. Again, a lower ratio of positives was seen with the urease test as compared to the PCR assay. Both assays scored positive for samples from one out of four gastric ulcer patients, and two of five esophagitis patients.

TABLE 3

Comparison of Various Assays for Detecting C. Pylori in Clinical Specimen

| Patient Number | Clinical Diagnosis by Endoscopy | Urease Test | PCR[a] with Universal Primers | PCR with C. pylori Primers | DH[b] by C. pylori Probe C | Warthin Starry Stain | Bacterial culture | Code |
|---|---|---|---|---|---|---|---|---|
| 1 | Normal | − | − | − | − | − | − | 3186940 |
| 2 | Duodenal Ulcer | + | + | + | + | + | + | 2272757 |
| 3 | Esophageal Ulcer | − | + | − | + | − | − | 1504704 |
| 4 | Duodenal Ulcer | + | + | + | + | + | − | 2978211 |
| 5 | Gastritis | − | − | − | − | − | − | 0566236 |
| 6 | Gastritis | − | + | + | − | − | − | 3161660 |
| 7 | Gastritis | + | + | + | + | NT[c] | − | 1961223 |
| 8 | Gastritis | − | + | + | − | − | − | 1466717 |
| 9 | Gastritis | + | + | + | + | + | + | 2254174 |
| 10 | Gastritis | + | + | + | − | NT | + | 3130427 |

[a]PCR = Polymerase Chain Reaction
[b]DH = Dot Blot Hybridization using the oligonucleotide probe designated C
[c]NT = Not Tested
For a description of the assays used see Materials and Methods.

TABLE 4

A Comparison of the Ratios of Positive Results Obtained Using the Urease Test and the PCR with C. Pylori Primers

| Clinical Diagnosis | Urease Test | PCR with C. pylori Primers |
|---|---|---|
| Gastritis | 5/10 | 7/10 |
| Gastric Ulcer | 1/4 | 1/4 |
| Duodenal Ulcer | 3/6 | 4/6 |
| Esophagitis | 2/5 | 2/5 |
| Esophageal Ulcer | 0/1 | 0/1 |
| Esophageal Cancer | 0/1 | 0/1 |
| Giardiasis | 0/1 | 0/1 |
| Normal | 0/3 | 0/3 |

No. of Positive Cases/Total No. of Cases Tested
For details see Materials and Methods

DISCUSSION

Figure 5:
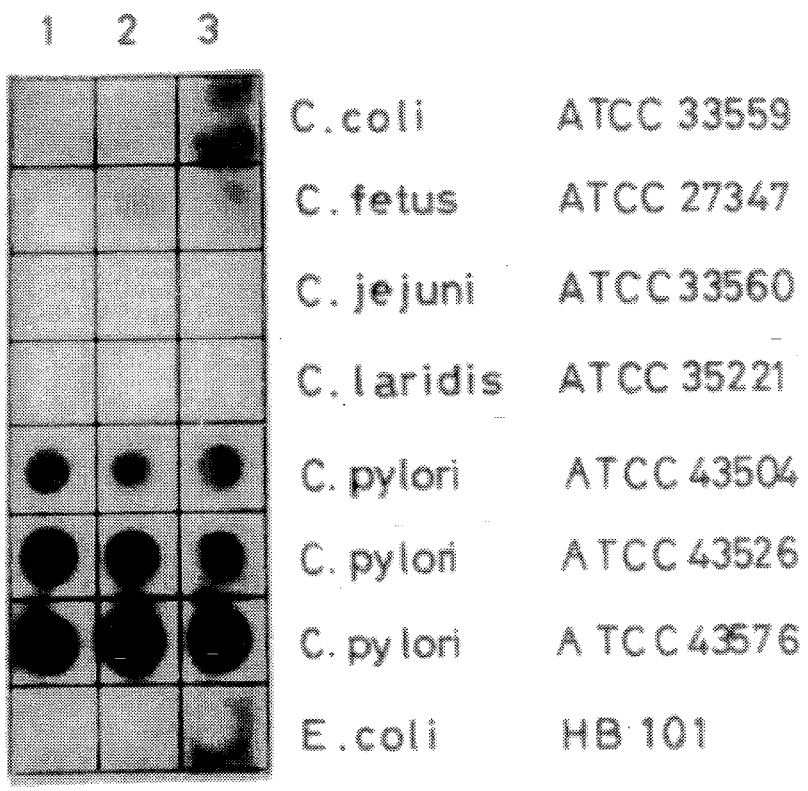
FIG. 5 Photograph Showing the Specificity and Sensitivity of DNA-RNA Dot Blot Hybridization. Results obtained with various bacterial species. In lane 1, each spot contained the equivalent of 6.25 μl of the indicated bacterial suspension ($OD_{660}$=2.5), lane 2 contained 12.5 μl and lane 3 contained 25 μl.
Figure 6:
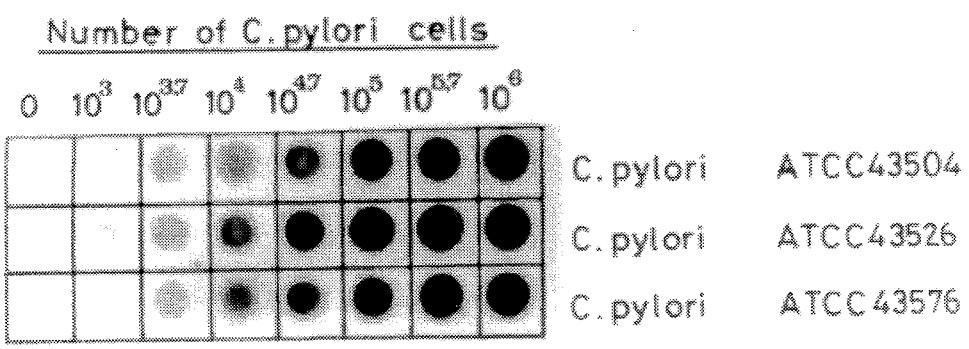
FIG. 6 Photograph Showing the Specificity and Sensitivity of DNA-RNA Dot Blot Hybridization. Results obtained with increasing amounts of three different strains of *C. pylori*. The amount of bacterial lysate per spot is expressed as the equivalent number of cells.

The phylogenetic study of bacteria has given rise to a taxonomic picture based on "oligonucleotide cataloging" of bacterial 16S rRNA sequences. By focusing on hypervariable sequences within these oligonucleotide catalogs, synthetic probes can be designed for use in diagnostic tests. We have found 22 nucleotide-long probes to be sufficient for species-specific hybridization in RNA dot blot experiments (see FIGS. 5 and 6). Theoretically, under the conditions used in these experiments, a two nucleotide mismatch is enough to preclude hybridization of the C. pylori probe CPC to RNA from other bacterial species. In this vein, a computer search of Gen Bank sequences was unable to turn up known bacterial sequences, other than C. pylori, that diverge from the hybridization probe CPC by two or fewer nucleotides. However, probe CPC hybridized to a biopsy sample from patient 3 in Table 2, which also gave rise to amplified fragments using the universal PCR primers. On the other hand this sample was negative in both the urease test and the C. pylori specific PCR assay. This suggests a correlation between the presence of a presently unknown bacterial species and the esophageal ulcer from this patient.

While DNA-RNA dot blot hybridization appears to have higher specificity for the detection of C. pylori than does DNA—DNA hybridization, the PCR assay supersedes both of these methods in ease and sensitivity (see Table 2). PCR amplification of bacterial 16S rDNA sequences using universal 16S rDNA primers can be used to detect the presence of bacteria in general (see FIG. 7) (SEQ ID NO: 4 and SEQ ID NO: 5), while C. pylori primers CPB and C sense can be used to specifically detect C. pylori. It follows that by examining the 16S rRNA oligonucleotide catalogs of other bacterial species, primers specific to these strains can also be designed.

The relative simplicity of the PCR detection method holds great clinical promise in the field of diagnosis. Amplification of bacterial sequences can be performed in as little as four hours for 30 cycles or two hours for 15 cycles. Additionally, only minute biopsy specimens are necessary for analysis. While polyacrylamide gel electrophoresis is presently used to analyze the amplified products, the development of colorimetric assays can further simplify this procedure. Using PCR techniques similar to the one developed here for detection of C. pylori, assays for the detection of various types of pathogenic bacteria in physiologic fluids such as blood and cerebrospinal fluid could be developed. Furthermore, variations in the PCR assay could be designed for the noninvasive detection of specific bacteria from feces, urine, and bronchial washings. This methodology could be extremely useful in the general area of infectious disease.

From the results presented in Tables 2 and 3, a comparison of the assays for the detection of C. pylori can be made. Dot blot hybridization appears to be the least sensitive, while the urease test, though rapid, has been shown to sporadically generate false negative results. The C. pylori specific PCR assay was able to amplify fragments not only in all of the samples scoring positive in the urease test, but in a few additional samples as well. Further studies are required, however, to rule out the possibility of a certain level of false positives in the PCR assay because of this extreme sensitivity.

The results we have obtained from PCR amplification of gastric biopsy specimens using C. pylori-specific primers support the correlation between the presence of C. pylori and gastritis, duodenal ulcers, and also esophagitis. A model consistent with these observations would involve the spread of C. pylori in the upper digestive tract, resulting in erythema, hemorrhage, and inflammation of mucous membranes. The toxicological reason for these responses is presently unknown. Nevertheless, the present studies suggest that the use of PCR amplification of clinical samples to detect C. pylori could prove to be valuable in the diagnosis of certain gastrointestinal diseases and as a guide to appropriate treatment.

EXAMPLE 3

UNIVERSAL AND SPECIFIC SEQUENCES

Examination of sequences of 1542 pairs of 16SrRNA in *E. coli* shows that in several locations there are strain-specific sequences and universal sequences common not only to *E. coli* but to all other bacteria.

In addition to *E. coli*, common universal sequences are found in the following strains: *Staphylococcus aureus* ATCC 25923, *S. auricularis* JCM2421, *S. sciure* JCM2425, *S. capitis* ATCC 27840, *S. cohnii* ATCC 29974, *S. epidermides* ATCC 14990, *S. haemolyticus* ATCC 29970, *S. hominis* ATCC 27844, *S. hyicus subsp, hyuicus* ATCC 11249, *S. intermedius* ATCC 29663, *S. saprophyticus* ATCC 15305, *S. simulans* ATCC 27848, *S. warneri* ATCC 27836, *S. xylosus* ATCC 29971, *S. lentus* JCM2426, *Pseudomonas cepacia, Salmonella typhi murium, S. typhi, S. enteritidis, S. london, Shigella flexneri, S. bovdii, S. sonnei, Campylobacter coli* ATCC 33559, *C. laridis* ATCC 35221, *C. jejuni* ATCC 3560, *C. fetus* ATCC 27347, *C. concisus* ATCC 33237, *C. cinaedi* ATCC 35683, *C. fennelliae* ATCC 35684, *Wollinela recta* ATCC 33238, *W. curva* ATCC 35224, *Helicobacter pylori* ATCC 43526, *Borrelia burqdorferri Sulfolobus*.

Gene Bank reports have also identified the presence of universal sequences in *Mycoplasma hyponeumoniae, Archaeoglobus fulgidus, Chlamydia psittasi, Halobacteria halobium, H. volcanii* and *Halococcus morrhua*. The universal sequence, composed of about 20 base pairs, surround alternating gene sequences or strain-specific sequences of 400–500 base pairs thereby forming 16SrRNA of about 1500 base pairs. These 16SrRNA are enclosed as such in the DNA.

Figure 16:
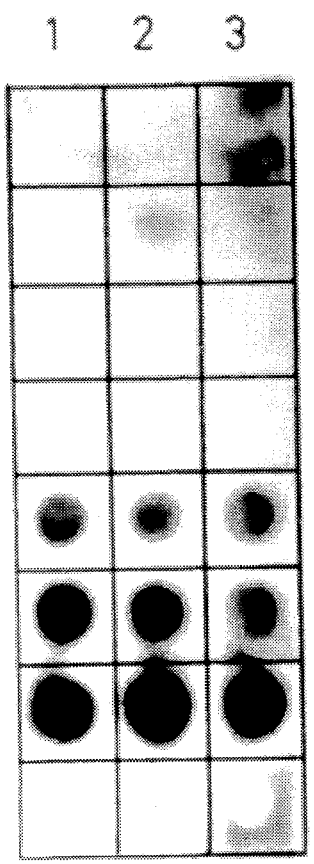
FIG. 16 Photograph showing the results of the examination of a portion of a strain-specific sequence. DNA was extracted from E. coli, Campylobacter and Helicobacter, then, absorbed onto a nylon membrane. This absorbed DNA was then hybridized with an oligonucleotide probe obtained from strain-specific sequence of 16SrDNA in Helicobacter. It is recognized that this probe can hybridize with only Helicobacter (25). In this way, a probe could be selected from 16SrDNA sequence which is capable of discriminating between Helicobacter and Campylobacter which two strains are said to be extremely closely related.

FIG. 16 is a photograph showing the results of an experiment which involved hybridizing an oligonucleotide probe obtained from a strain-specific sequence of 16SrDNA to target DNA. Such target DNA was extracted from *E. coli*, Campylobacter and Helicobacter and absorbed onto a nylon membrane. The DNA so absorbed was then hybridized with an oligonucleotide probe obtained from strain-specific sequence of 16SrDNA in Helicobacter. It is recognized that this probe can hybridize only with Helicobacter. The result of such hybridization is a probe from the 16SrDNA sequence which is capable of specifically recognizing and binding only Helicobacter. Such probe could then be an effective tool to distinguish between two closely related microbial strains, i.e. Helicobacter and Campylobacter.

After hybridizing such oligonucleotide probe to the strain specific sequences of Helicobacter, sequences including strain-specific sequence can be amplified by polymerase chain reaction (PCR) using two selected universal sequences as primers.

FIG. 17 is a photograph of a gel showing gene amplification of *Helicobacter pylori* using 16SRRI and 16SRRII obtained from the universal sequences of 16SrDNA as the chain terminals for PCR. FIG. 17 also shows the results of amplifying each strain of Staphylococcus and Pseudomonas using 16SRRI and 16SRRIV by PCR. These results show that the primers derived from the universal sequence are hybridized with 16SrDNA of different strains to cause gene amplification. Such primer DNAs may be synthesized with a DNA synthesizer. Applied Biosystems Inc. (ABI) has developed a technique which has facilitated the synthesis of oligomers considerably. Alternatively, "PCR Mate" is a commercially available device useful for the synthesis of primers in PCR technology. Because PCR Mate permits the synthesis of five to six primers of 20 base pairs in one day, the use of this device makes it considerably easy to synthesize DNA.

Experiments were carried out on the preparation of a probe specific for *H. pylori* using *H. pylori* and closely related strains. *H. pylori* has been recently attracting notice as the bacteria which causes gastric peptic ulcers.

Figure 18:
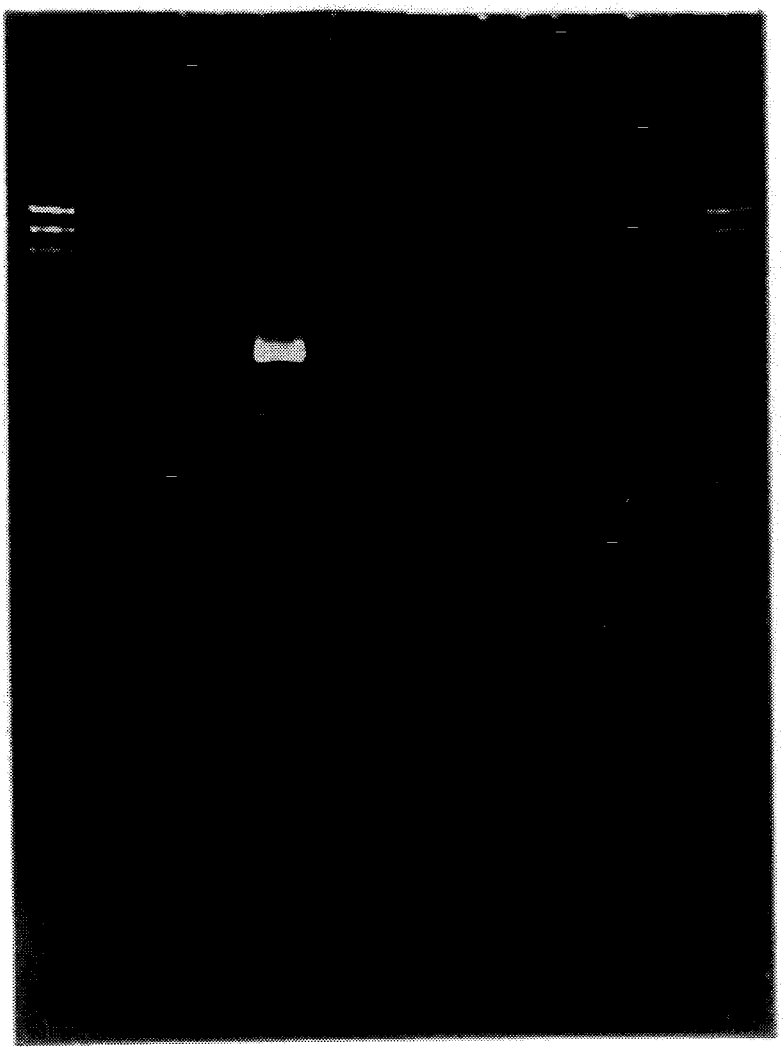
FIG. 18. Photograph showing an amplified gene using a primer CPI (5'GCG CAA TCA GCG TCA GGT AAT G 3') (SEQ ID NO: 2) and CP2 (5'GCT AAG AGA TCA GCC TAT GTC C 3') (SEQ ID NO: 3) both specific to 16SrDNA of H. pylori.

The protocol for preparing a probe specific for *H. pylori* is as follows. First, the sequence of 16SrDNA specific to *H. pylori* was determined by PCR using the universal sequence of 16SrDNA as a primer. Then an oligomer primer which is specific for *H. pylori* was synthesized from the sequence of 16 SrDNA so determined. The resulting synthesized oligomer primer was then used in another round of amplification by PCR. This experiment confirmed that only the DNA of *H. pylori* would participate in gene amplification (FIG. 18). Further, it was found that the amplification of DNA also occurred in samples containing cells destroyed by repeated freezing and thawing of colonies.

CLINICAL APPLICATION

Examination of clinical samples was conducted using a universal primer to detect the general presence of bacteria followed by the use of a strain-specific primer useful for detecting the specific presence of *H. pylori*. This experiment was designed to examine the effect of chemical treatment agents on bio-specimens taken directly from the stomach of patients and to determine whether or not ulcers had formed as a result of infection of *H. pylori*. The stomach biospecimens were frozen and thawed repeatedly, i.e. five times, then subjected to PCR using a universal primer. As a result, 12 of 31 specimens scored positive. This method makes it possible to detect the presence of bacteria other than *H. pylori*, in that a universal primer is used, so DNA would multiply, if any bacteria were present in the specimens.

The technique disclosed herein is useful for expediting the examination of specimens, such as blood or cerebrospinal fluid which are intrinsically located in aseptic environments, and the subsequent determination of the presence of bacteria in such specimens.

An experiment comparing the different means to detect *H. pylori* from clinical samples derived from ten patients with the following diagnostics was performed:

(1) an universal primer;

(2) a primer specific to *H. pylori;*

(3) a conventional culture technique;

(4) an argentation technique, said technique being a pathological one; and (5) a urease test.

The results of such an experiment is as follows. The argentation technique proved less sensitive compared to the *H. pylori*-specific-primer PCR technique. The conventional culture technique showed poor results because no medium suited to *H. pylori* has been developed at present. The urease test shows strong positivity due to the infection of *H. pylori* and high sensitivity, results approximately consistent with those of the PCR technique. The material resulting from patients who had been clinically diagnosed as having gastritis or gastric ulcer tested positive in PCR specific to *H. pylori*. On the basis of these results, it appeared that the PCR technique in which the primer specific to *H. pylori* was employed can be applied clinically.

PRACTICAL SEQUENCING TECHNIQUE

As previously mentioned, universal primers are effective as part of a method for examining the presence of bacteria (or other microbial agents) in samples, such as blood and cerebrospinal fluid, which samples are intrinsically found in aseptic environments. Moreover, in situations where there is an established relationship between a microbial strain and a particular disease, e.g. H. pylori and gastritis, expedited identification of a microbial agent and diagnosis of a potential infection is possible through the employment of a specific primer targeting a particular microbial strain.

The following method is a practical approach for detecting microbial agents (i.e. infectious agents) in samples taken from aseptic environments. Specifically, a universal primer is used to detect and hybridize to a target DNA sequence and such DNA is later amplified by PCR. Subsequently, strain-specific sequences are used to particularly recognize and bind to a target DNA sequence in order to amplify, by PCR, the DNA sequence so bound thereby permitting identification of the particular strain.

Identification of a particular strain can be achieved easily by determining the sequences of 16SrDNA of a variety of strains before detecting microbial agents, inputing the determined sequences into a computer program, and matching the sequence in question with the input data.

Clearly, the use of sequencing techniques is important for DNA examination in the field of bacteriology. The following is a description of the method for sequencing a desired nucleotide sequence. First, PCR is carried out with the universal primer of 16SrDNA (e.g. 16SRRI, and 16SRRII) to produce a number of DNA pieces of the same length as templates. Next, one of the primers used above (e.g. 16SRRII) is bound at its 5' terminal position with four colored fluorescent dyes separately through an aminolink 2 (ABI). Adenosine (A), thymine (T), cytosine (C) and guanine (G) are placed in four tubes, each in the form of a dideoxynucleotide, and the chain termination of the DNA synthesis which has been started from the above-mentioned primer is set off. The materials in these four tubes are combined into one tube and the combined material is subjected to the DNA automatic sequencer sold by ABI, that is, it is subjected to polyacrylamide gel electrophoresis followed by the detection of the specific wave length of each fluorescent dye by irradiation of halogen laser, thereby providing a readout of the sequence of the samples.

As set forth above, DNA pieces labeled with the four fluorescent dyes of different lengths are obtained, the resulting pieces are then subjected to electrophoresis and the sequences read out one after the other. FIG. 4 (SEQ ID NO: 1) shows the results obtained by reading out the sequences which result from linking the sequences of universal primers 16SRRII and M13, taken as primers of the sequences with four fluorescent dyes. This example uses 16SrDNA of S. aureus as a sample. At the time of electrophoresis and readout, measures are taken so that matching of the profile of DNA sequence of a variety of strains previously input into a computer with the profile of the sample is carried out simultaneously, and thus, electrophoresis is ceased as soon as a match with a sequence of a particular strain is found, with no need to continue further sequencing. That is to say, at that point, the identification of the strain will have been completed.

The difficult point of this method, however, is that, of the four fluorescent dyes (2 based on fluorescein isothiocyante (FITC) and 2 based on rhodamine), the excitation luminous capacity of the rhodamine-based fluorescent dyes is very weak, and even if these rhodamin-based dyes were employed in a concentration double that of the other dyes, sufficient excitation luminous capacity could not be achieved. Therefore, it seems that the development of fluorescent dyes of strong emission capacity will become an important issue.

SPECIFICITY OF DNA-RNA DOT BLOT HYBRIDIZATION (FIG. 16)

DNA-RNA dot blot hybridization was carried out by synthesizing an oligomer probe (5'GGA CAT AGG CTG ATC TCT TAGC3' SEQ ID NO: 1) complementary to 16SrRNA of H. pylori. This hybridization was conducted on each of the E. coli, Campylobacter, and Helicobacter pylori strains. The oligomer pieces were labeled with [$^{32}$P] dATP and polynucleotide kinase. Unreacted nucleotides were removed through a Sephadex G 50 spin column.

Strain liquid of $OD_{660}$=2.5 and RNA was extracted with GDE buffer (5M quinidine thiocyanate, 10 mM dithiothreitol, 0.1M EDTA pH=7.0). A nylon membrane filter (Gerne, Screen Plus) was spotted by a microsample filter-fold (minifold I). Lane 1 was spotted 6.25 μ,l Lane 2 12.5 μ,l and Lane 3 25 μ. Hybridization and washing were conducted following the procedure of Farr et al. Namely, a filter was incubated at 50° C. for 30 minutes in a hybridization solution (5M tetramethylammonium chloride, 50mM tris-solution (pH 7.5), 2mMEDTA, 0.3% SDS, 100 μg/ml denatured salmon sperm DNA, 5×Denhart's solution), after which a probe (10 ng/ml) was added to the incubated solution, and further incubated at 50° C. for 2 hours. Washing was carried out twice at room temperature for 10 minutes with 2×SSPE (1×SSPE:150mMNaCL, 0.1% SDS, 10 mM $NaH_2PO_4$, 1 mM EDTA) and twice again at 55° C. for 15 minutes with the hybridization solution (except for Salmon sperm DNA and Denhardt solution).

Figure 17A:
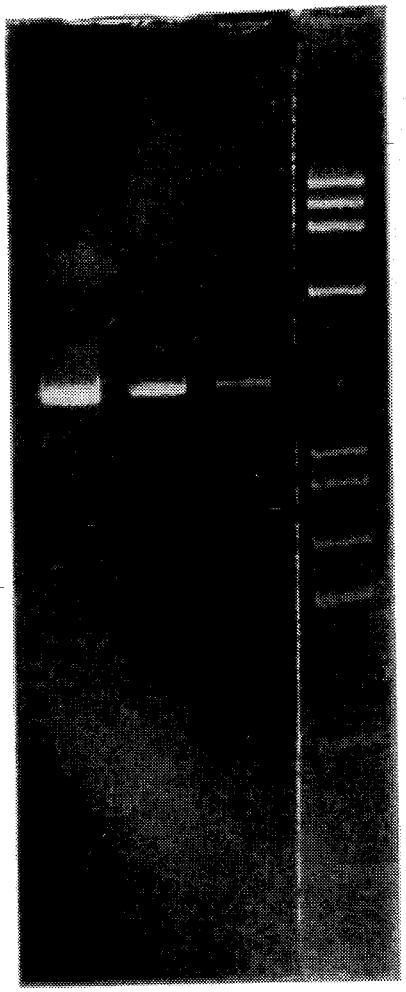
FIG. 17A Photograph of a gel showing an amplified gene using universal primer 16SRRI (5'CAG CAG CCG CGG TAA TAC 3') (SEQ ID NO: 5), corresponding to the 519–536th 16SrRNA of E. coli and 16SRRII (5'CCG TCA ATT CCT TTG AGT TT 3') (SEQ ID NO: 6), (corresponding to the 907–926th).
Figure 17B:
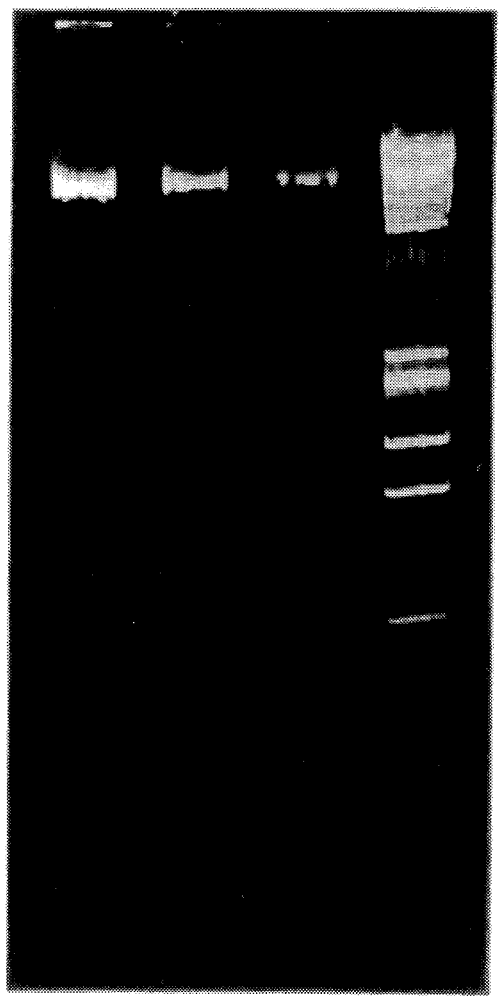
FIG. 17B Photograph of a gel showing an amplified gene using the universal primer of 16SRRI and 16SRRIV (5'ACG GGC GGT GTG TGC 3') (SEQ ID NO: 4), corresponding to 1313–1327 of 16SrRNA of E. coli.

GENE AMPLIFICATION OF 16SrDNA WITH A UNIVERSAL PRIMER (FIGS. 17A-B)

FIG. 17A shows the gene amplification with a universal primer 16SRRI (5'CAG CAG CCG CGG TAA TAC 3') (SEQ ID NO: 5), corresponding to the 519–536th 16SrRNA of E. coli and 16SRRII (5'CCG TCA ATT CCT TTG AGT TT 3') (SEQ ID NO: 6), (corresponding to the 907–926th).

Lane 1 contains a sample which comprises H. pylori ATCC 43504. Lane 2 contains a sample which comprises H. pylori ATCC 43526. Lane 3 contains a sample which comprises H. pylori ATCC 43576. Lane 4 contains a sample which comprises a DNA size marker (Hae III digestedφ×174 DNA). The size of the amplified DNA is about 400 base pairs.

FIG. 17B shows the gene amplification with the universal primer of 16SRRI and 16SRRIV (5'ACG GGC GGT GTG TGC 3') (SEQ ID NO: 4), corresponding to 1313–1327 of 16SrRNA of E. coli.

Lane 1 contains a sample which comprises Staphylococcus aureus ATCC 25923. Lane 2 contains a sample which comprises S. epidermidis ATCC 14990. Lane 3 contains a sample which comprises Pseudomonas cepacia. Lane 4 contains a sample which comprises a DNA size maker (Hae III digestedφ×174 DNA). The size of the amplified DNA is about 800 base pairs.

A strain suspension (10 μl) which has been subjected to repeated freezing and thawing was added to the reaction liquid (90 μl), comprising 1×PCR buffer (50 mM KCl, 10 mM Tris-HCL, pH 8.3, 1.5 mM $MgCl_2$, 0.01% (w/v) gelatin), 1.25 mM dNTPs, 100 ng of each primer, and 2.5 units of TaqDNA polymerase. Mineral oil was then stratified to the resultant liquid. PCR was carried out by the repetition thirty times of the following cycle: 94° C. for 1 minute, 55°–60° C. for 2 minutes, and at 72° C. for 3 minutes. The resultant amplified DNA was subjected to electrophoresis with 6% polyacrylamide gel and dyed with ethidium bromide.

STRAIN-SPECIFIC GENE AMPLIFICATION
(FIG. 18)

FIG. 18 shows the gene amplification with a primer CPI (5'GCG CAATCA GCG TCA GGTAAT G 3' (SEQ ID NO: 2) and CP2 (5'GCT AAG AGA TCA GCC TAT GTC C 3' (SEQ ID NO: 3) both specific to 16SrDNA of H. pylori.

Lanes 1 and 10 contain samples which comprise a DNA size maker (Hae III digested φx174 DNA). Lane 2 contains a sample which comprises a negative control, i.e. buffer. Lane 3 contains a sample which comprises E. coli DHI. Lane 4 contains a sample which comprises H. pylori ATCC 43504. Lane 5 contains a sample which comprises Campylobacter concisus ATCC 33237. Lane 6 contains a sample which comprises C. cinaedi ATCC 35683. Lane 7 contains a sample which comprises C. fennelliae ATCC 35684. Lane 8 contains a sample which comprises Wolinella recta ATCC 33238. Lane 9 contains a sample which comprises W. curva ATCC 35224. A strain suspension (10 µl) which has been subjected to repeated freezing and thawing was added to the reaction liquid (90 µl), comprising 1×PCR buffer (50 mM KCl, 10 mM Tris-HCL, pH 8.3, 1.5 mM $MgCl_2$, 0.01% (w/v) gelatin), 1.25 mM dNTPs, 100 ng of each primer, and 2.5 units of TaqDNA polymerase. Mineral oil was then stratified to the resultant liquid. PCR was carried out by the repetition thirty times of the following cycle: 94° C. for 1 minute, 55°–60° C. for 2 minutes, and at 72° C. for 3 minutes. The resultant amplified DNA was subjected to electrophoresis with 6% polyacrylamide gel and dyed with ethidium bromide.

Figure 19A:
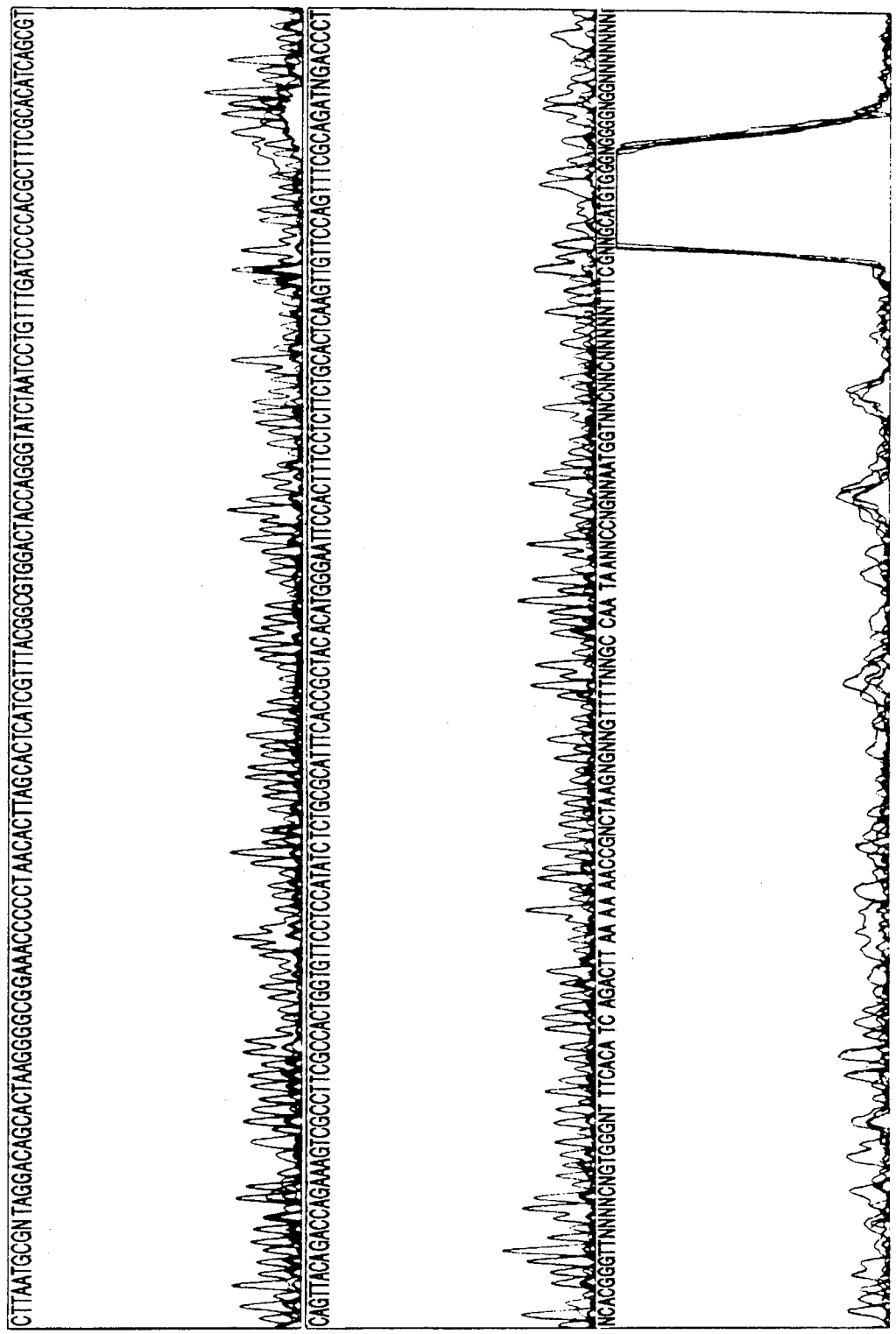

16SrDNA SEQUENCE OF STAPHYLOCOCCUS
ATC 25923 AFTER DNA AMPLIFICATION
(FIGS. 19A–B)

The DNA sequencer 373A from ABI was employed. A,C,T and G of the primer were labelled with a fluorescent dye FAM, JOE, TAM RA and ROX respectively through Aminolink 2. The chain extension reaction by Taq polymerase was ceased by adding ddNTP of each base into the four test tubes. Further, in place of GTP, 7-deaza-2'-deoxyguanosine-5'-triphosphate was employed. The reaction solution was prepared by adding a template DNA (1.5 µl) from PCR amplification to the following mixture to the volume of 15 µl:

MIXTURE

2 µl d/ddNTP Mix (ABI News Bulletin)

2 µl primer (0.4 pmole/µl)

9.5 µl 5×Taq dilution liquid (1×Taq dilution liquid: 0.1 unit/µl Taq polymerase, 50mM NaCl, 10 mM Tris-HCl, pH 8.5 and 10 mM $MgCl_2$ The reactions of G and T were effected in double volume, thereby fortifying the fluorescent emission.

Mineral oil (20 µl) was stratified. The sequence reaction was completed in 30 cycles of the following: 98° C. for 1 second, 60° C. for 2 seconds and 70° C. for 2 minutes.

REFERENCES

1. Saiki, R. K., Gelfand, D. H., Stoffel, S., Scharf, S. J., Higuchi, R., Horn, G. T., Mullis, K. B., and Erlich, H. A. 1988. Primer-directed enzymatic amplification of DNA with a thermostable DNA polymerase. Science 239:487–491.

2. Olsen, G. J., Lane, D. J., Giovannoni, S. J., et al. 1986. Microbial ecology and evolution: A ribosomal RNA approach. Ann. Rev. Microbiol. 40:337–365.

3. Lane, D. J., Pace, B., Olsen, G. J., Stahl, D. A., Sagin, M. L., and Pace, N. R. 1985. Rapid determination of 16S ribosomal RNA sequences for phylogenetic analyses. Proc. Natl. Acad. Sci. USA 82:6955–6959.

4. Edward, F. D., Wickham, G. S., and Pace, N. R. 1989 Phylogenetic stains: Ribosomal RNA-based probe for the identification of single cells. Science; 243:1360–1363.

5. Marshall, B. J., Warren, J. R., 1984. Unidentified curved bacilli in the stomach of patients with gastritis and peptic ulceration. Lancet i: 1311–1315.

6. Romaniuk, P. J., Zoltowska, B. T. J. Trust, D. J. Lane, G. J. Olson, N. R. Pace, and D. A. Stahl. 1987. Campylobacter pylori, the spiral bacterium associated with human gastritis, is not a true Campylobacter sp. J. Bacteriol. 169:2137–2141.

7. Blaser, M. J. 1987. Gastric Campylobacter-like organisms, gastritis, and peptic ulcer disease. Gastroenterol. 93:371–383.

8. Rauws, E. A. J., Langenberg, W., Hauthoff, H. J., Zanen, H. C., and Tytgat, G. N. J., 1988. Campylobacter pylordis-associated chronic active antral gastritis. Gastroenterology 94:33–40.

9. Humphreys, H., S. Bourke, C. Dooley, D. McKenna, B. Power, C. T. Keane, E. C. Sweeney, and C. O'Morian. 1988. Effect of treatment on Campylobacter pylori in peptic disease: a randomized prospective trail. Gut. 29:279–283.

10. Borromeo, M., J. R. Lambert, and K. J. Pinkard. 1987. Evaluation of "CLO"-test to detect Campylobacter pyloridis in gastric mucosa. J. Clin. Pathol. 40:462–463.

11. Engstrand, L., C. Pahlson, S. Gustavsson, and A. Schwan. 1986. Monoclonal antibodies for rapid identification of Campylobacter pyloridis. Lancet 1:1402–1403.

12. Hazell, S. L., T. J. Borody, A. Gal., and A. Lee. 1987. Campylobacter pyloridis gastritis I: Detection of urease as a marker of bacterial colonization and gastritis. Am. J. Gastroenterol. 82:292–296.

13. McNulty, C. A. M., and R. Wise. 1985. Rapid diagnosis of Campylobacter-associated gastritis. Lancet i:1443–1444.

14. Gen-Probe, 1986. 2 Mycoplasma T. C. II rapid detection system package insert.

15. Edelstein, P. H., 1986. Evaluation of the Gen-Probe DNA Probe for the detection of Legionellae in culture. J. Clin. Microbiol. 1986: 481–484.

16. Sommerfelt, H., K. H. Kalland, P. Raj, S. L. Moseley, M. K. Bhan, and B. Bjorvant. 1988. Cloned polynucleotide and synthetic oligonucleotide probes used in colony hybridization are equally efficient in the identification of enterotoxigenic Escherichia coli. J. Clin. Microbiol. 26:2275–2278.

17. Farr, C. J., R. K. Saiki, H. A. Erlich, F. McCormick, and C. J. Marshall. 1988 Analysis of RAS gene mutation in acute myeloid leukemia by polymerase chain reaction and oligonucleotide probes. Proc. Natl. Acad. Sci. USA 85:1629–1633.

18. Morotomi, M., T. Ohno, and M. Mutai. 1988. Rapid and correct identification of Bacteroides spp. with chromosomal DNA probes by whole-cell dot blot hybridization. Appl. Environ Microbiol. 54:1158–1162.

19. Tompkins, L. S., and Krajden, M. 1986. Approaches to the detection of enteric pathogens, including Campylobacter, using nucleic acid hybridization. Diagn. Microbiol. Infect. Dis. 4:71s–78s.

20. Rashtchian, et al. 1986. Abstract No. C-90. Abstracts of the Annual Meeting of the American Society for Microbiology:343.

21. Higuchi, R., von Beroldingen, C., Sensabaugh, and H. Erlich, 1988. Nature 332:543–546.

22. Saiki, R. K., Scharf, S., Faloona, F., Mullis, K. B., Horn, G. T., Erlich, H. A., and N. Arnheim, 1985. Enzymatic amplification of b-globin genomic sequences and restriction site analysis for diagnosis of sickle cell anemia. Science 230:1350–1354.

23. Lennette, E. H., Balows, A., Hausler W. J., and H. J. Shadomy, 1985. Manual of Clinical Microbiology, Fourth Edition. (Washington, D.C., American Society for Microbiology).

24. Jiang W., Kahn, S. M., Guillem, J., et al. 1989. Rapid detection of ras oncogenes in human tumors: Applications to colon, esophageal, and gastric cancer. Oncogene 4:923–928.

What is claimed is:

1. A method for detecting the presence of *Campylobacter pylori* ribosomal DNA in a sample of isolated DNA comprising:

a) contacting the sample with a DNA oligomer having the sequence 5'GCGCAATCAGCGTCAGGTAATG3' (SEQ ID NO:2) and a DNA oligomer having the sequence 5'GCTAAGAGATCAGCCTATGTCC3' (SEQ ID NO:3) under conditions suitable for a polymerase chain reaction so as to amplify the DNA encoding *Campylobacter pylori* 16s ribosomal RNA sequences lying between the binding sites of the DNA oligomers; and b) detecting the amplified DNA encoding *Campylobacter pylori* 16s ribosomal RNA sequences lying between the binding sites of the DNA oligomers, thereby detecting the presence of *Campylobacter pylori* ribosomal DNA in the sample.

2. The method of claim 1, wherein the detection in step b) comprises:

i) isolating the amplified *Campylobacter pylori* DNA encoding 16s ribosomal RNA by gel electrophoresis and visualizing the DNA by staining the gel with ethidium bromide and exposing the ethidium bromide-stained gel to ultraviolet light; or ii) isolating the amplified *Campylobacter pylori* DNA encoding 16s ribosomal RNA and visualizing the DNA by a colorimetric assay.

3. A method according to claim 1 for a germ-free clinical test for detecting the presence of *Campylobacter pylori* ribosomal DNA in a sample, further comprising maintaining the sample under sterile conditions.

4. The method of claim 1, wherein the isolated DNA sample is derived from a tissue specimen.

5. A method according to claim 1 for a germ-free clinical test for the diagnosis of gastritis associated with *Campylobacter pylori* in a subject wherein the isolated DNA sample is derived from gastric tissue of the subject.

6. A method of detecting the presence of *Campylobacter pylori* in a cell sample, comprising:

a) contacting the sample with an agent capable of lysing the *Campylobacter pylori* and then with the DNA oligomer 5'GGACATAGGCTGATCTCTTAGC3' (SEQ ID NO:1) labeled with a detectable marker selected from the group consisting of a radiolabelled molecule, a fluorescent molecule, an enzyme, and a ligand, so as to produce a hybrid consisting of the DNA oligomer and complementary *Campylobacter pylori* 16s ribosomal RNA sequences;

b) removing unbound DNA oligomer; and c) detecting the hybrid by means appropriate to the type of marker with which the DNA oligomer is labelled, thereby detecting the presence of *Campylobacter pylori* in the sample.

7. A method according to claim 6 for a germ-free test for detecting in a sample the presence of *Campylobacter pylori*, further comprising maintaining the sample under sterile conditions.

8. The method of claim 6 wherein the sample is a tissue specimen.

9. A method according to claim 8 for a germ-free clinical test for the diagnosis of gastritis associated with *Campylobacter pylori* in a subject, wherein the tissue specimen is gastric tissue.

10. The method of claim 6 further comprising, after step b), quantitating the amount of *Campylobacter pylori* 16s ribosomal RNA present in the sample by means appropriate to the type of marker used.

11. A method for a germ-free clinical test for detecting the presence of *Campylobacter pylori* in a tissue specimen which comprises:
   a) homogenizing the specimen in the presence of an agent capable of lysing the *Campylobacter pylori* under sterile conditions;
   b) contacting the resulting sterile tissue homogenate with two or more DNA oligomers complementary to the sense or antisense strand of DNA encoding the species-specific bacterial or protozoan 16s ribosomal RNA and useful as polymerase chain reaction primers under conditions suitable for a polymerase chain reaction, so as to amplify DNA encoding species-specific 16s ribosomal RNA of the specific bacterium or protozoan to be detected present between the hybridizing sites of the DNA oligomers; and
   c) contacting the specimen from step b) with a membrane filter so as to bind the amplified ribosomal DNA in the tissue homogenate to the filter;
   d) contacting the then resulting membrane filter with the DNA oligomer 5'GGACATAGGCTGATCTCTTAGC3' (SEQ ID NO:1) labelled with $^{32}$P-labelled 2',3'-dideoxyadenosine 5'-triphosphate under conditions such that the DNA oligomer forms a hybrid with complementary *Campylobacter pylori* 16s ribosomal DNA sequences;
   e) removing unbound DNA oligomer; and
   f) detecting the presence of *Campylobacter pylori* 16S ribosomal DNA sequences by detecting the resulting $^{32}$P-labelled hybrid on the filter,
   thereby detecting the presence of *Campylobacter pylori* in the tissue specimen.

12. A method according to claim 11 for a germ-free clinical test for diagnosing gastritis associated with *Campylobacter pylori*, wherein the tissue specimen is gastric tissue.

13. A method for detecting the presence of *Campylobacter pylori* in a sample, comprising:
   a) treating the sample with an agent capable of lysing the *Campylobacter pylori*;
   b) contacting the lysed sample with two or more DNA oligomers complementary to the sense or antisense strand of DNA encoding the *Campylobacter pylori* 16s ribosomal RNA and useful as polymerase chain reaction primers under conditions suitable for a polymerase chain reaction, so as to amplify DNA encoding *Campylobacter pylori*-specific 16s ribosomal RNA present between the hybridizing sites of the DNA oligomers;
   c) contacting the amplified DNA with the DNA oligomer 5=GGACATAGGCTGATCTCTTAGC3' (SEQ ID NO: 1) labelled with $^{32}$P-labelled 2',3'-dideoxyadenosine 5'-triphosphate so as to produce a labelled hybrid consisting of the DNA oligomer and complementary *Campylobacter pylori* 16s ribosomal RNA sequences;
   d) removing unbound DNA oligomer; and
   e) detecting the presence of the $^{32}$P marker on the labelled hybrid,
   thereby detecting the presence of *Campylobacter pylori* in the sample.

14. The method of claim 13, further comprising maintaining the sample under sterile conditions.

15. The method of claim 13, wherein the sample is a tissue specimen.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: Y ( x i ) SEQUENCE DESCRIPTION: SEQ ID NO:1:

GGACATAGGC TGATCTCTTA GC        22

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: Y ( x i ) SEQUENCE DESCRIPTION: SEQ ID NO:2:

GCGCAATCAG CGTCAGGTAA TG        22

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:3:

GCTAAGAGAT CAGCCTATGT CC                                                                              2 2

( 2 ) INFORMATION FOR SEQ ID NO:4:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:4:

ACGGGCGGTG TGTGC                                                                                      1 5

( 2 ) INFORMATION FOR SEQ ID NO:5:

( i ) SEQUENCE CHARACTERISTICS:
     ( A ) LENGTH: 18 base pairs
     ( B ) TYPE: nucleic acid
     ( C ) STRANDEDNESS: single
     ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:5:

CAGCAGCCGC GGTAATAC                                                                                   1 8

( 2 ) INFORMATION FOR SEQ ID NO:6:

( i ) SEQUENCE CHARACTERISTICS:
     ( A ) LENGTH: 20 base pairs
     ( B ) TYPE: nucleic acid
     ( C ) STRANDEDNESS: single
     ( D ) TOPOLOGY: linear ( i i ) MOLECULE TYPE: DNA (genomic)

( i i i ) HYPOTHETICAL: N ( i v ) ANTI-SENSE: Y ( x i ) SEQUENCE DESCRIPTION: SEQ ID NO:6:

CCGTCAATTC CTTTGAGTTT                                                                                 2 0

( 2 ) INFORMATION FOR SEQ ID NO:7:

( i ) SEQUENCE CHARACTERISTICS:
     ( A ) LENGTH: 195 base pairs
     ( B ) TYPE: nucleic acid
     ( C ) STRANDEDNESS: double
     ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:7:

ATCTTGCGAC CGTACTCCCC AGGCGGGATG CTTAATGCGT TACGTGCATT ACTGGAGAGA          6 0
CTAAGCCCTC CAACAACTAG CATCCATCGT TTAGGGCGTG GACTACCAGG GTATCTAATC          1 2 0

```
CTGTTTGCTC  CCCACGCTTC  GCGCAATCAG  CGTCAGGTAA  TGTTCAGCAG  GTCGCCTTCG      180

CAATGAGTAT  TCCTG                                                            195
```

( 2 ) INFORMATION FOR SEQ ID NO:8:

( i ) SEQUENCE CHARACTERISTICS:
        ( A ) LENGTH: 401 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:8:

```
CTTAATGCGN  TAGGACAGCA  CTAAGGGGCG  GAAACCCCCT  AACACTTAGC  ACTCATCGTT       60

TACGGCGTGG  ACTACCAGGG  TATCTAATCC  TGTTTGATCC  CCACGCTTTC  GCACATCAGC      120

GTCAGTTACA  GACCAGAAAG  TCGCCTTCGC  CACTGGTGTT  CCTCCATATC  TCTGCGCATT      180

TCACCGCTAC  ACATGGGAAT  TCCACTTTCC  TCTTCTGCAC  TCAAGTTGTT  CCAGTTTCGC      240

AGATNGACCC  TNCACGGGTT  NNNNCNGTGG  GNTTCACAT   CAGACTTAAA  AAACCGNCTA      300

AGNGNNGTTT  TNNGCCAATA  ANNCCNGNNA  ATGGTNNCNN  CNNNNNTTTC  GNNGCATGTG      360

GGNGGGGNGG  NNNNNNNNNN  GGNNNGCGNN  NNNNNNNNNG  G                           401
```